United States Patent [19]
Lee et al.

[11] Patent Number: 6,025,539
[45] Date of Patent: Feb. 15, 2000

[54] IL-5 TRANSGENIC MOUSE

[75] Inventors: James J. Lee; Nancy A. Lee, both of Scottsdale, Ariz.

[73] Assignee: Mayo Foundation for Medical Education and Research, Rochester, Minn.

[21] Appl. No.: 08/629,643

[22] Filed: Apr. 9, 1996

[51] Int. Cl.$^7$ .............................. C12N 5/00; C12N 15/00; C12N 15/09

[52] U.S. Cl. ...................... 800/2; 435/172.3; 435/69.1; 435/69.52; 435/91.2; 435/320.1; 435/325; 536/23.5; 536/24.31; 424/9.2

[58] Field of Search .............................. 800/2; 435/172.3, 435/69.1, 69.52, 91.2, 320.1, 325; 536/23.5, 24.31; 424/9.2

[56] References Cited

PUBLICATIONS

Lee et al., Journal of Immunology, vol. 158:3, pp. 1332–1344, Feb. 1, 1997.

Houdebine, Journal of Biotechnology, vol. 34, pp. 269–287, 1994.

Anderson, European Respiratory Review, vol. 5:29, pp. 231–237, 1995.

Fuggar, L., et al., "Expression of HLA–DR4 and Human CD4 Transgenes in Mice Determines the Variable Region β–chain T–cell Repertoire and Mediates an HLA–DR–restricted Immune Response", *Proc. Natl. Acad. Sci. USA*, 91, 6151–6155 (Jun. 1994).

Bourke, P.F., et al., "Localization of the Inducible Enhancer in the Mouse Interleukin–5 Gene That is Responsible to T–Cell Receptor Stimulation", *Blood*, 85, 2069–2077 (Apr. 1995).

Nakajima, H., et al., "CD4$^+$ T–Lymphocytes and Interleukin–5 Mediate Antigen–Induced Eosinophil Infiltration into the Mouse Trachea", *American Review of Respiratory Disease*, 146, 374–377, (Aug., 1992).

Oshiba, A., et al., "Pretreatment with Allergen Prevents Immediate Hypersensitivity and Airway Hyperresponsiveness", *Am. J. Respir. Crit. Care Med.*, 153, 102–109, (Jan., 1996).

Blyth, D.I., et al., "Lung Inflammation and Epithelial Changes in a Murine Model of Atopic Asthma", *Am. J. Respir. Cell Mol. Biol.*, 14, 425–438, (1996).

Brusselle, G., et al., "Allergen–Induced Airway Inflammation and Bronchial Responsiveness in Wild–Type and Interleukin–4–Deficient Mice", *Am. J. Respir. Cell Mol. Biol.*, 12, 254–259, (1995).

Corry, D.B., et al., "Interleukin 4, but Not Interleukin 5 or Eosinophils, Is Required in a Murine Model of Acute Airway Hyperreactivity", *J. Exp. Med.*, 183, 109–117, (Jan., 1996).

Foster, P.S., et al., "Interleukin 5 Deficiency Abolishes Eosinophilia, Airways Hyperreactivity, and Lung Damage in a Mouse Asthma Model", *J. Exp. Med.*, 183, 195–201, (Jan., 1996).

Hackett, B.P., et al., "Cell–Specific Expression of a Clara Cell Secretory Protein–Human Growth Hormone Gene in the Bronchiolar Epithelium of Transgenic Mice", *Proc. Natl. Acad. Sci. USA*, 89, 9079–9083, (Oct., 1992).

Hamelmann, E., et al., "Requirement for CD8$^+$ T Cells in the Development of Airway Hyperresponsiveness in a Murine Model of Airway Sensitization", *J. Exp. Med.*, 183, 1719–1729, (Apr., 1996).

Iwamoto, T., et al., "Evaluation of Airway Hyperreactivity in Interleukin–5 Transgenic Mice", *Intl. Arch. Allergy Immunol.*, 108 (Suppl. 1), 28–30, (Sep., 1995).

Lefort, J., et al., "Effect of Antigen Provocation of IL–5 Transgenic Mice on Eosinophil Mobilization and Bronchial Hyperresponsiveness", *J. Allergy Clin. Immunol*, 97, 788–799, (Mar., 1996).

K. Georgopoulos, et al., "A T Cell–Specific Enhancer is Located in a DNase I–Hypersensitive Area at the 3' End of the CD3–delta Gene", *EMBO J.*, 7, 2401–2407 (1988).

P. van den Elsen, et al., "Exon/Intron Organization fo the Genes Coding for the Delta Chains of the Human and Murine T–Cell Receptor/T3 Complex", *Proc. Natl. Acad. Sci. USA*, 83, 2944–2948 (May, 1986).

L. A. Dent, et al., "Eosinophilia in Transgenic Mice Expressing Interleukin 5", *J. Experimental Medicine*, 172, 1425–1431, (Nov., 1990).

K. Tohyama, et al., "Establishment of an Interleukin–5–Dependent Subclone from an Interleukin–3–Dependent Murine Hemopoietic Progenitor Cell Line, LyD9, and its Malignant Transformation by Autocrine Secretion of Interleukin–5", *EMBO J.*, 9, 1823–1830, (1990).

A. Tominaga, et al., "Transgenic Mice Expressing a B Cell Growth and Differentiation Factor Gene (Interleukin 5) Develop Eosinophilia and Autoantibody Production", *J. Experimental Medicine*, 173, 429–437, (Feb., 1991).

*Primary Examiner*—Jasemine C. Chambers
*Assistant Examiner*—Jill D. Schmuck
*Attorney, Agent, or Firm*—Schwegman, Lunderberg, Woessner & Kluth, P.A.

[57] ABSTRACT

A transgenic mouse is provided, the cells of which contain and express IL-5 in a cell type- or tissue-specific manner and in an amount which results in an IL-5-associated pathology. Also provided are expression cassettes comprising an IL-5 gene, operably linked to a cell type- or tissue-specific transcriptional control sequence and methods of using transgenic mice comprising the expression cassettes.

19 Claims, 23 Drawing Sheets

(5 of 23 Drawing Sheet(s) Filed in Color)

| age (months) | mouse | Percentage marrow cell types | | | | | Eosinophil lineage cells/femur (X 10⁻⁶) | | | |
|---|---|---|---|---|---|---|---|---|---|---|
| | | total cells/femur (X 10⁻⁶) | erythroblast | mononuclear | eosinophil | neutrophil | Class I | Class II | Class III | Class IV |
| 1 | +/+ | 24.08 (2.90)⁴ | 35.50 (17.59) | 29.33(15.37) | 3.38(1.60) | 31.33(8.81) | 0.08(0.05) | 0.09 (0.04) | 0.39 (0.22) | 0.35 (0.23) |
| | NJ.1638 | 17.12 (3.02)⁶ | 9.17 (1.72) | 8.50 (3.07) | 70.50(7.87) | 11.83(4.51) | 0.20 (0.13) | 0.69 (0.37) | 3.50 (1.45) | 7.98 (2.08) |
| 4 | +/+ | 32.65(13.85)³ | 39.66(8.14) | 25.34 (8.13) | 2.75 (1.31) | 31.74 (8.31) | 0.12 (0.06) | 0.08 (0.03) | 0.34 (0.14) | 0.42 (0.24) |
| | NJ.1638 | 31.65 (3.60)⁴ | 8.02 (4.99) | 11.41 (4.49) | 66.18(6.59) | 14.39 (5.16) | 0.61 (0.09) | 1.45 (0.45) | 6.08 (0.73) | 13.05(2.53) |
| 10 | +/+ | 43.97 (6.79)³ | 37.76 (4.77) | 19.63 (2.47) | 3.16 (1.74) | 39.45 (8.92) | 0.25 (0.18) | 0.08 (0.05) | 0.65 (0.43) | 0.74 (0.52) |
| | NJ.1638 | 33.23(4.58)⁴ | 6.03 (4.17) | 9.33 (2.33) | 71.75(9.16) | 12.89 (3.78) | 0.53 (0.16) | 1.05 (0.52) | 5.55(3.14) | 17.30 (1.13) |

FIG. 5A

| age (months) | mouse | Percentage spleen cell types ||||| Eosinophil lineage cells/femur (X $10^{-6}$) ||||
|---|---|---|---|---|---|---|---|---|---|---|
| | | total cells/spleen (X $10^{-7}$) | erythroblast | mononuclear | eosinophil | neutrophil | Class I | Class II | Class III | Class IV |
| 1 | +/+ | 17.50 (3.64)[3] | 21.17 (6.81) | 72.83(8.04) | 0.33(0.29) | 5.67(1.04) | 0.01(0.01) | <0.01 | 0.02 (0.02) | 0.03 (0.03) |
| | NJ.1638 | 97.40 (7.20)[4] | 28.88(2.14) | 19.38(2.36) | 48.25(2.75) | 3.50(1.47) | 0.85 (0.46) | 1.40 (0.44) | 12.27 (2.71) | 33.23 (5.65) |
| 4 | +/+ | 18.63(4.05)[3] | 19.99(13.99) | 76.14(15.90) | 0.62(0.80) | 3.25(2.60) | 0.03 (0.03) | 0.01 (0.01) | 0.02 (0.02) | 0.13 (0.17) |
| | NJ.1638 | 311.40 (120.49)[4] | 16.98(7.49) | 27.38(10.78) | 51.31(8.09) | 4.26(4.69) | 2.25 (1.29) | 8.56 (5.02) | 56.18 (24.17) | 92.69(28.51) |
| 10 | +/+ | 20.33 (2.32)[3] | 14.50(7.37) | 80.17(8.52) | 0.33 (0.29) | 4.83(1.53) | 0.01 (0.01) | <0.01 | 0.01 (0.01) | 0.05 (0.04) |
| | NJ.1638 | 387.67(118.00)[3] | 8.00(3.46) | 40.50(7.40) | 47.50(7.50) | 4.00(3.00) | 4.30 (2.78) | 7.12(4.41) | 60.72(37.50) | 122.13 (46.95) |

FIG. 5C

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

ACCCCACACC TAGCCCACTG          20

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

TGGCAGTGGC CCAGACACAG C          21

(2) INFORMATION FOR SEQ ID NO:3:

(i) SEQUENCE CHARACTERISTICS:
      (A) LENGTH: 1560 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:3:

CGGGATTTTG CTGCCTTACC ACAGCCCAAA GCAGGCTGTG TGTTTAGAAG CTGAGCCACA    60

AAGAAGTTTC CATGACATCA TGAATGGGGG TGGCAGAGAA GAATATTGGG GCTCAGAGGG   120

TGTGTGTGTG TGTGTGTGTG TGTGTGTGTG TGTGTGTGTG AGAGAGAGAG AGAGAGAGAG   180

```
AGAGAGAGAG AGACAGACAG AGAGACAGAG AGACAGAAAG ACAGAAAGAC AGAAAGACAG    240

AGACAGAGCT GTCAAGAATT TTCTTCTACT TCGTGGGTTC TGGGGATTGT ACTAAGGTCA    300

TGAGGCTTGT GTGGCAAGCA CCCTTACCCA CTGAGCCATC TTGCCTGCCC TCATCCTCAA    360

ATTAATTAAA AATAAAGAAC ATGATGAATT GACGCCAGTG CCAAGCTAGC GGCCGCGGTC    420

CAACCACCAA TCTCAAAGCT TGCATGCCTG CAGGTCGACT CTAGAGGATC AGCCAGGGTT    480

TAGCACTATC CTCCGCCAAC AGACTCATGG GTATTCAGAA AAAGGAAGAG TGGGGAGGA     540

ACTAGAAGAA ATCTGCCTCT CTACCTTCTG CCTTTGATGG TGTAAGACTG TCAAAGCAAC    600

AGTGGGCTAG GTGTGGGGTA AGACACAAAC AGGTGCAAAC TGCTCTTTCT GAAGCAAAGA    660

GTTTGGGATG ATTGATACAA AGCAGAGACT ATGCATGGAT CCGAATTCAT CATGTTCCTT    720

TATTTTTAAT TAATTTGAGG ATGAGGGCAG GCAAGATGGC TCAGTGGGTA CCACGATTGA    780

GAAGAAAATC TTGACAGCTC TGTCTCTGTC TTTCTGTCTT TCTGTCTTTC TGTCTCTCTG    840

TCTCTCTGTC TGTCTCTCTC TCTCTCTCTC TCTCTCTCTC TCTCACAC ACACACACAC     900

ACACACACAC ACACACACAC ACACCCTCTG AGCCCCAATA TTCTTCTCTG CCACCCCCAT    960

TCATGATGTC ATGGAAACTT CTTTGTGGCT CAGCTTCTAA ACACCACACC TGCTTTGGGC   1020

TGTGGTAAGG CAGCAAAATC CCGGAAGTTG TTATGATAGG GACTGGAACC AACAGGCAAT   1080

GAAGCAGAGT GGCTGGGCTG ACCCTGCCCA CGGAAACCCA CAGGGTTAGA AATGCCAAGG   1140

GGCCAGGATG GGAAGCTGTC CCTCGTACTG CCTGTCTGGG TCTGAGGAGA GGAAGCCAGA   1200

AGTGAGGGGC CACGGGTGGG CAGAACTCAG CCAAGCTAAG ACAACTCTCA ATCCATGCTT   1260

TGGAAAACAC AGGCGCGGAT CCTCACATCC CAATCCGCGG CCGCAATTCG TAATCATGGA   1320

ACAAACTTTC CTCATAGTCT CTGCTTTGTA TCAATCATCC CAAACTCTTT GCTTCAGAAA   1380

GAGCAGTTTG CACCTGTTTG TGTCTTACCC CACACCTAGC CCACTGTTGC TTTGACAGTC   1440

TTACACCATC AAAGGCAGAA GGTAGAGAGG CAGATTTCTT CTAGTTCCTC CCCCACTCTT   1500

CCTTTTCTG AATACCCATG AGTCTGTTGG CGGAGGATAG TGCTAACCCT GGCTGATCAT    1560

(2) INFORMATION FOR SEQ ID NO:4:

(i) SEQUENCE CHARACTERISTICS:
        (A) LENGTH: 1534 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: mat_peptide
        (B) LOCATION: 104...442
        (D) OTHER INFORMATION:

(xi) SEQUENCE DESCRIPTION: SEQ ID NO:4:

CGCTCTTCCT TTGCTGAAGG CCAGCGCTGA AGACTTCAGA GTCATGAGAA GGATGCTTCT     60

GCACTTGAGT GTTCTGACTC TCAGCTGTGT CTGGGCCACT GCCATGGAGA TTCCCATGAG    120

CACAGTGGTG AAAGAGACCT TGACACAGCT GTCCGCTCAC CGAGCTCTGT TGACAAGCAA    180

TGAGACGATG AGGCTTCCTG TCCCTACTCA TAAAAATCAC CAGCTATGCA TTGGAGAAAT    240

CTTTCAGGGG CTAGACATAC TGAAGAATCA AACTGTCCGT GGGGGTACTG TGGAAATGCT    300

ATTCCAAAAC CTGTCATTAA TAAAGAAATA CATTGACCGC CAAAAGAGA AGTGTGGCGA     360

GGAGAGACGG AGGACGAGGC AGTTCCTGGA TTACCTGCAA GAGTTCCTTG GTGTGATGAG    420
```

```
TACAGAGTGG GCAATGGAAG GCTGAGGCTG AGCTGCTCCA TGGTGACAGG ACTTCACAAT    480

TTAAGTTAAA TTGTCAACAG ATGCAAAAAC CCCACAAAAC TGTGCAAATG CAAGGGATAC    540

CATATGCTGT TTCCATTTAT ATTTATGTCC TGTAGTCAGT TAAACCTATC TATGTCCATA    600

TATGCAAAGT GTTTAACCTT TTTGTATACG CATAAAAGAA ATTCCTGTAG CGCAGGCTGG    660

CCTCAAACTG GTAATGTAGC CAAGGATAAC CTTGAATTTC TGATCCTCCT GCCTCCTCTT    720

CCTGAAGGCT GAGGTTACAG ACATGCACCA TTGCCACTAG TTCATGAAGT GCTGGAGATG    780

GAACCCAAGG CTTTGTGCAT GTTACCAACT GAGTTATACT CCCTCCCCCT CATCCTCTTC    840

GTTGCATCAG GTCTCAAGT ATTCCAGGCT GACTTTGAAC TCAGTGTGTA GCCAAGGGTG     900

ACCCTGAACT CTTGGTCCAG ATGGACGCAG GAGGATCACA TACCCAACCT TAGCATCCTT    960

TCTCCTAGCC CCTTTAGATA GATGATACTT AATGACTCTC TTGCTGAGGG ATGCCACACC   1020

GGGGCTTCCT GCTCCTATCT AACTTCAATT TAATACCCAC TAGTCAATCT CTCCTCAACT   1080

CCCTGCTACT CTCCCCAAAC TCTAGTAAGC CCACTTCTAT TTCTTGGGGA GAGAGAAGGT   1140

TGACTTTTCT TATGTCCTAT GTATGAATCA GACTGTGCCA TGACTGTGCC TCTGTGCCTG   1200

GAGCAGCTGG ATTTTGGAAA AGAAAAGGGA CATCTCCTTG CAGTGTGAAT GAGAGCCAGC   1260

CACATGCTGG GCCTTACTTC TCCGTGTAAC TGAACTTAAG AAGCAAAGTA AATACCACAA   1320

CCTTACTACC CCATGCCAAC AGAAAGCATA AAATGGTTGG GATGTTATTC AGGTATCAGG   1380

GTCACTGGAG AAGCCTCCCC CAGTTTACTC CAGGAAAAAC AGATGTATGC TTTTATTTAA   1440

TTCTGTAAGA TGTTCATATT ATTTATGATG GATTCAGTAA GTTAATATTT ATTACAACGT   1500

ATATAATATT CTAATAAAGC AGAAGGGACA ACTC                               1534

(2) INFORMATION FOR SEQ ID NO:5:

(i) SEQUENCE CHARACTERISTICS:
        (A) LENGTH: 6727 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: mat_peptide
        (B) LOCATION: 650...3771
        (D) OTHER INFORMATION: Join 650..730, 1560..1592,
            3468..3596, 3676..3771

(xi) SEQUENCE DESCRIPTION: SEQ ID NO:5:

TGTACCTCCC ACATCTGCTG GTGTGTACCA CCACACCTAG TAAGATATTC TCAACATTTA     60

TGTATTTTAG CCTAACCCTG TTGGAGGTAT ACATTTGAAT ACATTTTTTC TCACTTTATC    120

AGGAATTGAG TTTAACACAT ATTAAAGCAG GTGTGGGGCA GGGAGGGGGG GATAAAAAAG    180

AAGGTGCTCA AGAAAAGCCG ATCACGCTCC CAAGAGTGTG AGCATGGGCG TCTCTAGAGA    240

GATCCGCCAT ATATGCACAA CTTTTAAAGA GAAATTCAAT AACCAGAATG GAGTGTAAAT    300

GTGGATCAAA GTTGTAGAAA CATTCTTTTA TGTTATAGAA AATGCTTTTT AAGCAGGGGT    360

GGGGGTCAAG ATGTTAACTA TTATTAAAGA GCAAAAAAAA AAAAATGCAT TTTGTTTGAA    420

GACCCAGGGC ACTGGAAACC CTGAGTTTCA GGACTCGCCT TTATTAGGTG TCCTCTATCT    480

GATTGTTAGC AATTATTCAT TTCCTCAGAG AGAGAATAAA TTGCTTGGGG ATTCGGCCCT    540

GCTCTGCGCT CTTCCTTTGC TGAAGGCCAG CGCTGAAGAC TTCAGAGTCA TGAGAAGGAT    600

GCTTCTGCAC TTGAGTGTTC TGACTCTCAG CTGTGTCTGG GCCACTGCCA TGGAGATTCC    660
```

```
CATGAGCACA GTGGTGAAAG AGACCTTGAC ACAGCTGTCC GCTCACCGAG CTCTGTTGAC    720

AAGCAATGAG GTAAAGTATA ACTTATTCCT TCAGCTTTGT TTTTAAGATC AGGACCTTGC    780

TATACCGCTC TGACTGGCCT CAAACTTGCT ATGTAGGGTA GGCTGTCCTA ACCCCTACCA    840

GATCTCCTTA CCTATGTCTC CCAAATACTA GGATTACAGA CACATTACCT TGCCTGACGC    900

TATGGTTCTT CAGAATGCAT AAATAGCTGC ATTTGGCCTT TAATCCCAGA ACTTGGGAGG    960

CAGGGTCAGG TGGATCTCTG TGAGTTCAAG GCCAGACTTG TCTACGTGGC CAGTTACAGG   1020

ACAGCCAGAG CTAAAGCAAG ACCCTGATTC AAAATAATTT TTTTTCAAAA CAAAAAAAAA   1080

AAACCCAAAC CATTTGTGGC AATTCATTTC TAAACATAAA GATCTGCTTT AAATAGTGCA   1140

ATTATGGCTT GTTCCCTTGC CTTCTTGCTC CCGTTCTGTC CTCTTGTCCC ACTCTCTCCC   1200

CATTCCACCC CCACCATGTG CTCATGGCCC GCATCTCTAC TTCTCTACTC TCTTTCTCTC   1260

CCTCTCCCCT CCTTCTTCCT TTCCCTCTCT CTCTCCCTCT TCTTCTCCTC CTCTCTTTCT   1320

CTCTCTCTCC CTCTCTCTCT CTCTTTCTCT CTCTCTCTGC TTTTTTCTAT CTCTACTACC   1380

CTCTCAACTC CCCTCTCCAT GCCCTGAATA AGCTCTATTC TATACTAAAA AAAAAAAGT    1440

GCAATTATGA ATGTGTTAGT GTTAATGCAC AGGTGATAAC CCTATCACCA GCAAGCATTG   1500

CATTAAAAAA GGCAACGGAC TCTCTTTAGG ATGACCCTAT GATGTTCTTT CCTTTGCAGA   1560

CGATGAGGCT TCCTGTCCCT ACTCATAAAA ATGTAAGTTA TTCTTTACTG CCGTGCTTGC   1620

ATGAGTAAGT CAGCTTCGCA TACTAAGCTA TAAGTCATCT GCATCTAGCT TTCTGGTGTT   1680

GTGTGTGTCT GGGATGGGGA CCTCTCTAGG TCTCAAGCTC CTGGGTTCAA GTGATTCTCT   1740

TGCCTTGATA GAGCAGCTGG GACACAGGCC TGTGCCACCA CACCCAGCAG AGCTTTTGAT   1800

TTCAGTTAAA CTGTTTGACT TTCTTGGAAA AGAAAATTTA TGTAGGTAGA TATGAAAGTT   1860

TGTGCTTATA AATAAAAAGA ATATGAGAGT GGCAAATTAT GTAATCCCAG TACTTGGGAG   1920

CCAAAGGCAG GGGTAGTCTG AGTCTAGGGC CAGCTTAGAT ACATTGCCCT GTATGTATCA   1980

AAAGTAAATC CTATAAATAA ATAAACAAAA ACATTAGAGG GCTGGAGATA TAAGCTCTGT   2040

TGATAGATGG CCTAATATGC TGGGTTGACT CTTAGCACCC CATAAACTAA ACATGGAAGT   2100

ACCTGGCTGT AATCTCATGA TGGTGAAATG GAGGCGGGAA GATCATAGGT TCAAGGTCAT   2160

CCTCAGCTAC ATTTTTGAGC TAGAGGCCAG CCTGGGCTAT GAGACACGCA AAAACCACCA   2220

GCCAATTAAT ATTAGGAATG GCTTTGAGCT AGATCTGTTA TGTAAGTGGC CAGCTGGAGC   2280

TGTCAGTCAT ACATCTCACA GCCTCACAAG ATTCTTTGCA TGGCGAGAGG TCCTGCTGGG   2340

CTCCCTTTGG CTCTGTCCAT GGCTCTCTTC ATCCTAGTGC CTCTCTTTGT TTTCCTTGTC   2400

TTATTTCTTA CTGCTGAGGA TCAAGCCCAG GGCCTTCAGT GTGTGAAGTG AGCACTCTAC   2460

CACTGAATTC CAGAGCCCGC CCACTCTAAT GCCTTTCTGA AGTATTAAG AGTTTAGGGT    2520

TATATATTCC TTTTGTTTAT TTTATGTGTA TGAGCATTTT GCCTGCATAT ATATATATAT   2580

ATATATATAT ATATATATAT GTGTGTGTGT GTGTGTGTGT GTGTGTATAT ATATATGTAT   2640

GTATGTATGT ATGTATGTAT GTATGTATAT GTGTGTGTGT GTGTGTGTGT GTGTGTGTGT   2700

GTTCCACGTA TGTGTCTATG TGTCTGGTGT TCCTGAAGGC TAAAAGAAGG GCATCAGATC   2760

ACCTGGGGCT GGATATGCAG ATGGTTGTGA GCCAACCATC TGGATGCTGG GAACTGCATC   2820

AAGTGTTCTT AACCACTGAG CCATCTCTCC CGCTCAGAGG GTTATATTCT TAGGTAATGA   2880

TAGAAAGACA TAAAAATATC ATGAATGCCT TTATTAATAA TTTCTAAACA GTTTAATGAA   2940

TATGACTATG TAGTGATATT GTATACATTT CAATATTATC TTATTCTAGC GTAAAGTACA   3000

TTATTTAACT TTTTCTAAAT AGAAGAAAAT TCATCAGCCT AAATTTCAAA AGAAAATATT   3060
```

-continued

```
AATATGGGTG TGGTACCACT CACCTTTAAT CCAGATGGTT GTGAGCCACC ACAAGGGTGC   3120

TGGTAACTGA ACCCAGGTCC TCTGGAAGAG GACCCAGTGA TCTTAACCAC TGAGCCATCT   3180

CCCCAGCCCC AATCCTAACT TTGGGTTCAT TTTTTTGAAA TGATCTCATG TAGCACTAGC   3240

TGGCCTCAAA CTCTATGTAT CAGAGGCTGG CCTTCAACTC CTGATCCTCT TACCTCAACT   3300

TCCTGAATGC TGGCATTACA GATAAGCACC ATCACATCTT GTATTGTCTG GGGTTTTTTA   3360

TTGATGCATT TAAATTGCAT GTATTTATTG CATATGGCAT GATATTTCAA AATATGTGTA   3420

CGTTGTGGGC AGTCTGATCT ATTTGCTTCT TGATAATCTT CTTTCAGCAC CAGCTATGCA   3480

TTGGAGAAAT CTTTCAGGGG CTAGACATAC TGAAGAATCA AACTGTCCGT GGGGGTACTG   3540

TGGAAATGCT ATTCCAAAAC CTGTCATTAA TAAAGAAATA CATTGACCGC CAAAAAGTAA   3600

GTTCCCCAGG GACCCTGTGA ATCCGGCTGC AGCTGGTTCT CCAGGAGCCA ACCTGACAGT   3660

CTGTTCTTTT CACAGGAGAA GTGTGGCGAG GAGAGACGGA GGACGAGGCA GTTCCTGGAT   3720

TACCTGCAAG AGTTCCTTGG TGTGATGAGT ACAGAGTGGG CAATGGAAGG CTGAGGCTGA   3780

GCTGCTCCAT GGTGACAGGA CTTCACAATT TAAGTTAAAT TGTCAACAGA TGCAAAAACC   3840

CCACAAAACT GTGCAAATGC AAGGGATACC ATATGCTGTT TCCATTTATA TTTATGTCCT   3900

GTAGTCAGTT AAACCTATCT ATGTCCATAT ATGCAAAGTG TTTAACCTTT TTGTATACGC   3960

ATAAAAGAAA TTCCTGTAGC GCAGGCTGGC CTCAAACTGG TAATGTAGCC AAGGATAACC   4020

TTGAATTTCT GATCCTCCTG CCTCCTCTTC CTGAAGGCTG AGGTTACAGA CATGCACCAT   4080

TGCCACTAGT TCATGAAGTG CTGGAGATGG AACCCAAGGC TTTGTGCATG TTACCAACTG   4140

AGTTATACTC CCTCCCCCTC ATCCTCTTCG TTGCATCAGG GTCTCAAGTA TTCCAGGCTG   4200

ACTTTGAACT CAGTGTGTAG CCAAGGGTGA CCCTGAACTC TTGGTCCAGA TGGACGCAGG   4260

AGGATCACAT ACCCAACCTT AGCATCCTTT CTCCTAGCCC CTTTAGATAG ATGATACTTA   4320

ATGACTCTCT TGCTGAGGGA TGCCACACCG GGGCTTCCTG CTCCTATCTA ACTTCAATTT   4380

AATACCCACT AGTCAATCTC TCCTCAACTC CCTGCTACTC TCCCCAAACT CTAGTAAGCC   4440

CACTTCTATT TCTTGGGGAG AGAGAAGGTT GACTTTTCTT ATGTCCTATG TATGAATCAG   4500

ACTGTGCCAT GACTGTGCCT CTGTGCCTGG AGCAGCTGGA TTTTGGAAAA GAAAAGGGAC   4560

ATCTCCTTGC AGTGTGAATG AGAGCCAGCC ACATGCTGGG CCTTACTTCT CCGTGTAACT   4620

GAACTTAAGA AGCAAAGTAA ATACCACAAC CTTACTACCC CATGCCAACA GAAAGCATAA   4680

AATGGTTGGG ATGTTATTCA GGTATCAGGG TCACTGGAGA AGCCTCCCCC AGTTTACTCC   4740

AGGAAAAACA GATGTATGCT TTTATTTAAT TCTGTAAGAT GTTCATATTA TTTATGATGG   4800

ATTCAGTAAG TTAATATTTA TTACAACGTA TATAATATTC TAATAAAGCA GAAGGGACAA   4860

CTCAAATTCA GTTTGCTATT GGTCTTTTCT AACCCTGGGT GTGTGCAGGG ACCCAGAGGA   4920

GAGACTGAGT ATGTCCTGAC TAAGCACTTT CAGCTCCTTA GAGCTTCAGG GAGCACCAAG   4980

GGTGGACTTG GTAGTGGTAT CGGGAGCAAG AACAAGGGCT GGGACTGAGC CTGGATCTCC   5040

CTATGTAGGA GTATGTCCAG ATGGCTCAGG GTGAACAGGA GAGGAATGAA TGAGAGGATG   5100

AATGAATGAA TGAATAAATG AATGAATGGG AGATCGCTCC ATTAATAAAG TGCTTGCTGT   5160

ACAAGGATGA AGAGCTGAGT TCGAGCTCCA AAACCCATTT CAGAAAGCTG GCATGGTGG    5220

GGGCACACTT GTAGTCCTGA CACTGGGAGA CAGAAATAGC CAGATCCCTG GGGCTCTCTG   5280

TTCAGCCAAC CTAAATGAAT TGGTGAGTTC TGGACCAGTG AGAGATCTTC TCTCAAAAAG   5340

CAAGGTGGAA GCCGAGCGTG GTGACACACG CCTTTAATTC CAGCACTTGG GAGGCAGAGG   5400
```

-continued

```
CAGGCGGATT TCTGAGTTCG AGGCCAGCCT GGTCTACAAA GTGAGTTCCA GGACAGCCAG    5460

GGCTACACAG AGAAACCCTG TCTCAAAAAA CAAACAAACA AACAAACAAA CAAACCACCA    5520

TGAACTACCT GTGTATGCAT GTTGTGTGTG CTTGCATTGT GCAGGTCAAA TGAACACACT    5580

GGGACTCTTC CACTAACACT CTCTACCTCG TTCCCTAAGA GGGTCTCCTG CTGAACATGG    5640

AGTTTCCCAT TTCTTTTGGT TAGGCTGGCA GCCAGCCAGC AAGTCCCAGC GATCCTCCTG    5700

TCTCCTCTTC CTCCTGCTCA GCCCCAGGGG TGGAGTCTTA GGTATGCGTG GCCATGCCAG    5760

GCTTTTTCCA TGGGTGCTGG AGATCCAGAC GCAGCTTCTC ATGTTCGCGC AGTGGCACTC    5820

TTGCCCACTG AAGCATCTTC CATCTTGCCC ACTGAAGCAT CTCCCATCTT ACCCACTCAA    5880

GCATCTTCCA TCTTACCCAC TCAAGCATCT TCCATCTTAC CCACTCAAG ATCTTCCATC     5940

TTACCCACTC AAGCATCTTC CAGCTCCTTA GTATGTTTTT TTTTTAAACA TGTACTTGGC    6000

TTTTTAAAAT TGTAATAAAC TAAAGGTATA CAATATGTAT TGATTGATAT GCTTACTTAT    6060

GTATTTATCT TTATTTTCTT ATTTTTTTAA AAAATTTATT TTATTTATAT GAATACACTG    6120

TAGCTGACTT CAGACACACC AGAACAGGGC ATTGGATCCC ATTACGGATG GTTGTGAGCC    6180

ACCATGTGGT TGCTGGGAAT TGAACTCAGG ACCTTTGGAA GAACAGTCTC TCTGGCTCTG    6240

TAGTTATCTT TCAGTATACT TTTCCTTGAA AATTTTATAT GTCTGTGCGA TCTATTCTGG    6300

TCCTACCATT CACTCTCACT CTTCCTGGAC TTCCCAGTAT GGCCCCCTCC CGATTTCAAA    6360

TCTTCTCACT CTTATTTTTT AGCCCACTGA GTTCAGTTAG TGTTGTCCCT ATGAGCACGT    6420

GTGGACCATC TACTTGAGCT TAGGCAACCT ACCAGTGGCC ACATCCCTAC AGGAAAGGTA    6480

CTCTTCCTCT CTTGGTGGCC ATAAACCCCC AACGGGTCCT CACATAGGGC AGGAGCCTTA    6540

GGAGTTTCCC TCCCCATTCA TACTAAACTT TGGTTGGCTT GATGGTGTGA AGATAACCAC    6600

AGCTGCTGTG AGGTCCTGAG TACAAGGGCC AAGTCACGTC CAGGAGGCAG CATCTCACAG    6660

TACTTACCCC CAGTCTCTGG CTCGAACATC CTTCCCACCA TCCCCCTTCA TCATGTTCCT    6720

TAAGCTT                                                              6727
```

IL-5 TRANSGENIC MOUSE

BACKGROUND OF THE INVENTION

The etiology of many respiratory diseases has remained unclear in spite of direct attempts to determine factors that lead to pulmonary damage and loss of function. Asthma is a respiratory disorder affecting both children and adults. It is a multifactorial syndrome characterized by breathlessness, pulmonary constriction, airway hyperreactivity and mucous accumulation. It is often, but not always associated with allergies (extrinsic) or environmental stimuli, e.g., tobacco smoke.

The common physiological manifestation of asthma is the temporary constriction of the airways. Cellular infiltrates of the airway epithelium of symptomatic individuals include lymphocytes as well as myeloid granulocytes (Busse et al., *Am. J. Respir. & Crit. Care Med.*, 152, 388 (1995)). Bronchoalveolar lavage (BAL) fluid or biopsies of lung tissue from affected individuals frequently show elevated levels of eosinophils, a myeloid leucocyte thought to play a role in host defense against parasitic infections.

Eosinophilia is characteristic of allergy and infection by helminths. One of the intriguing aspects of eosinophilia is its biological specificity, in which an increase in eosinophils can occur in the absence of increases in other leucocytes. In vitro data has suggested that the sequential action of interleukin-1(IL-1) and interleukin-3 (IL-3) or granulocyte stimulating factor (G-CSF) are necessary for eosinophil progenitor production while IL-5 is responsible only for the differentiation of progenitor cells into mature eosinophils (Sanderson et al., *J. Exp. Med.*, 162, 60 (1985); Yamaguchi et al., *J. Exp. Med.*, 167, 43 (1988); Clutterbuck et al., *Blood*, 75, 1774 (1990); Warren et al., *J. Immunol.*, 140, 94 (1988)). IL-5 is expressed primarily by T cells, although other cell types may express this cytokine.

To define the role of IL-5 in vivo, Dent et al. (*J. Exp. Med.*, 172, 1425 (1990)) made transgenic mice in which transcription of a genomic copy of the IL-5 gene was under the transcriptional regulatory influence of the dominant control region (DCR) of the gene encoding human CD2 (a T cell surface antigen). Although Dent et al. showed that serum IL-5 levels were elevated in transgenic mice (Tg5C2), because the CD2 enhancer element is only weakly active in mature peripheral T cells, the elevation in serum IL-5 levels was primarily due to thymocyte expression and not peripheral T cell expression. In contrast, serum IL-5 levels are elevated in parasite infested (*Mesocestroides corti*) or antigen challenged mice as a result of IL-5 expression by peripheral T cells. Moreover, despite the increase in serum IL-5 levels, the Tg5C2 mice showed no symptomatic effects of IL-5 overexpression other than a mild splenomegaly and an eosinophilia accompanying a 7-fold increase in white blood cell (WBC) count.

Tominaga et al. (*J. Exp. Med.*, 173, 429 (1991)) disclose that transgenic mice in which a IL-5 cDNA was linked to the mouse metallothionein promoter (Tg-6 mice) demonstrated a peripheral eosinophilia with a 3-fold increase in total WBCs. Serum IL-5 levels in Tg-6 mice were 16,000 pg/ml. The predominant sites of IL-5 expression in these mice were the kidney and liver. These organ sites are not normally associated with the production of IL-5 and thus fail to mimic the necessary microenvironmental cues that occur in peripheral sites. Thus, the lack of significant physiological effects in these mice may be the result of ectopically produced IL-5.

Thus, a need exists for an animal model that constitutively expresses IL-5 in a tissue and/or cell-type specific fashion. Moreover, a need exists for an animal model that constitutively expresses IL-5 in thymocytes and peripheral T cells, so as to result in IL-5 induced pathologies.

SUMMARY OF THE INVENTION

The invention provides a transgenic mouse whose cells incorporate a preselected chimeric DNA sequence which is integrated into the genome of the mouse and comprises a thymocyte and/or T cell specific transcription control sequence operatively linked to a DNA segment which encodes interleukin-5. The DNA segment which encodes interleukin-5 lacks endogenous interleukin-5 control sequences which are 5' to the interleukin-5 coding sequence. The DNA segment is expressed as interleukin-5 so as to result in eosinophil-associated pathologies in the transgenic mouse.

Also provided is a transgenic mouse whose cells incorporate a preselected chimeric DNA sequence which is integrated into the genome of the mouse and comprises a thymocyte and/or T cell specific transcription control sequence operatively linked to a DNA segment which encodes interleukin-5. The DNA segment lacks endogenous interleukin-5 control sequences which are 5' to the interleukin-5 coding sequence. The interleukin-5 encoded by the DNA segment is expressed in the serum of the transgenic mouse in an amount that is at least about fifty times, preferably at least about seventy-five times, more preferably at least about one hundred times, greater than the amount of interleukin-5 in the serum of a corresponding nontransgenic mouse.

Another embodiment of the invention is a transgenic mouse, the cells of which contain a preselected chimeric DNA sequence comprising a lung specific transcription control sequence operatively linked to a DNA segment which encodes interleukin-5. The preselected chimeric DNA sequence is integrated into the genome of the mouse. The DNA segment is expressed as interleukin-5 so as to result in eosinophil-associated pathologies.

Further provided is a transgenic mouse, the cells of which contain a preselected chimeric DNA sequence, which is integrated into the genome of the mouse, wherein said preselected chimeric DNA sequence comprises a lung specific transcription control sequence operatively linked to a DNA segment which encodes interleukin-5. The interleukin-5 encoded by the DNA segment is expressed in the transgenic mouse in an amount that is at least about fifty times, preferably at least about one hundred times, and more preferably at least about one thousand times, greater than the amount of interleukin-5 in a corresponding nontransgenic mouse.

Also provided is an expression cassette comprising a DNA segment encoding interleukin-5, which segment lacks endogenous interleukin-5 control sequences that are 5' to the interleukin-5 coding sequence. The DNA segment is operably linked to a thymocyte and/or T cell specific transcription control sequence.

Another embodiment of the invention is an expression cassette comprising a DNA segment encoding interleukin-5 operably linked to a lung specific transcription control sequence.

Also provided are methods of using the transgenic mouse of the invention. The method comprises expressing a chimeric DNA sequence, which is integrated into the genome of the transgenic mouse, in the cells of the transgenic mouse. The chimeric DNA sequence comprises a thymocyte and/or T cell specific transcription control sequence operatively linked to a DNA segment which encodes interleukin-5. The DNA segment lacks any endogenous interleukin-5 control sequences which are 5' to the interleukin-5 coding sequence. The DNA segment is expressed in the serum of the transgenic mouse in an amount of interleukin-5 that is at least about fifty times, preferably at least about seventy-five times, more preferably at least about one hundred times, greater than the amount of interleukin-5 in the serum of a corresponding nontransgenic mouse.

Further provided is a method of using a transgenic mouse which comprises expressing a chimeric DNA sequence in the cells of the transgenic mouse. The chimeric DNA sequence, which is integrated into the genome of the transgenic mouse, comprises a thymocyte and/or T cell specific transcription control sequence operatively linked to a DNA segment which encodes interleukin-5. The DNA segment lacks any endogenous interleukin-5 control sequences which are 5' to the interleukin-5 coding sequence. The DNA segment is expressed in an amount of interleukin-5 so as to result in eosinophil-associated pathologies in said transgenic mouse.

Yet another embodiment of the invention is a method of using a transgenic mouse which comprises administering an agent to the transgenic mouse. The transgenic mouse comprises a chimeric DNA sequence comprising a thymocyte and/or T cell specific transcription control sequence operatively linked to a DNA segment which encodes interleukin-5. The DNA segment lacks any endogenous interleukin-5 control sequences which are 5' to the interleukin-5 coding sequence. The chimeric DNA sequence is integrated into the genome of the mouse. The DNA segment is expressed as interleukin-5 in the transgenic mouse. Then it is determined whether said agent reduces or inhibits interleukin-5 expression in the transgenic mouse relative to a transgenic mouse which has not received the agent.

Further provided is a method of using a transgenic mouse which comprises expressing a chimeric DNA sequence in the cells of the transgenic mouse. The chimeric DNA sequence, which is integrated into the genome of the transgenic mouse, comprises a lung specific transcription control sequence operatively linked to a DNA segment which encodes interleukin-5. The DNA segment lacks any endogenous interleukin-5 control sequences which are 5' to the interleukin-5 coding sequence. The DNA segment is expressed in an amount of interleukin-5 so as to result in eosinophil-associated pathologies in said transgenic mouse.

Also provided is a method of using a transgenic mouse which comprises expressing a chimeric DNA sequence in the cells of the transgenic mouse. The chimeric DNA sequence, which is integrated into the genome of the transgenic mouse, comprises a lung specific transcription control sequence operatively linked to a DNA segment which encodes interleukin-5. The DNA segment is expressed in the transgenic mouse in an amount of interleukin-5 that is at least about fifty times, preferably at least about one humndred times, and more preferably at least about one thousand times, greater than the amount of interleukin-5 in a corresponding nontransgenic mouse.

Further provided is a method of using a transgenic mouse which comprises administering an agent to the transgenic mouse. The transgenic mouse comprises a chimeric DNA sequence, which is integrated into the genome of the transgenic mouse, comprising a lung specific transcription control sequence operatively linked to a DNA segment which encodes interleukin-5. The DNA segment is expressed as interleukin-5 in the transgenic mouse. It is then determined whether said agent reduces or inhibits interleukin-5 expression in the transgenic mouse relative to a transgenic mouse which has not received the agent.

DETAILED DESCRIPTION OF THE INVENTION

Figure 1:
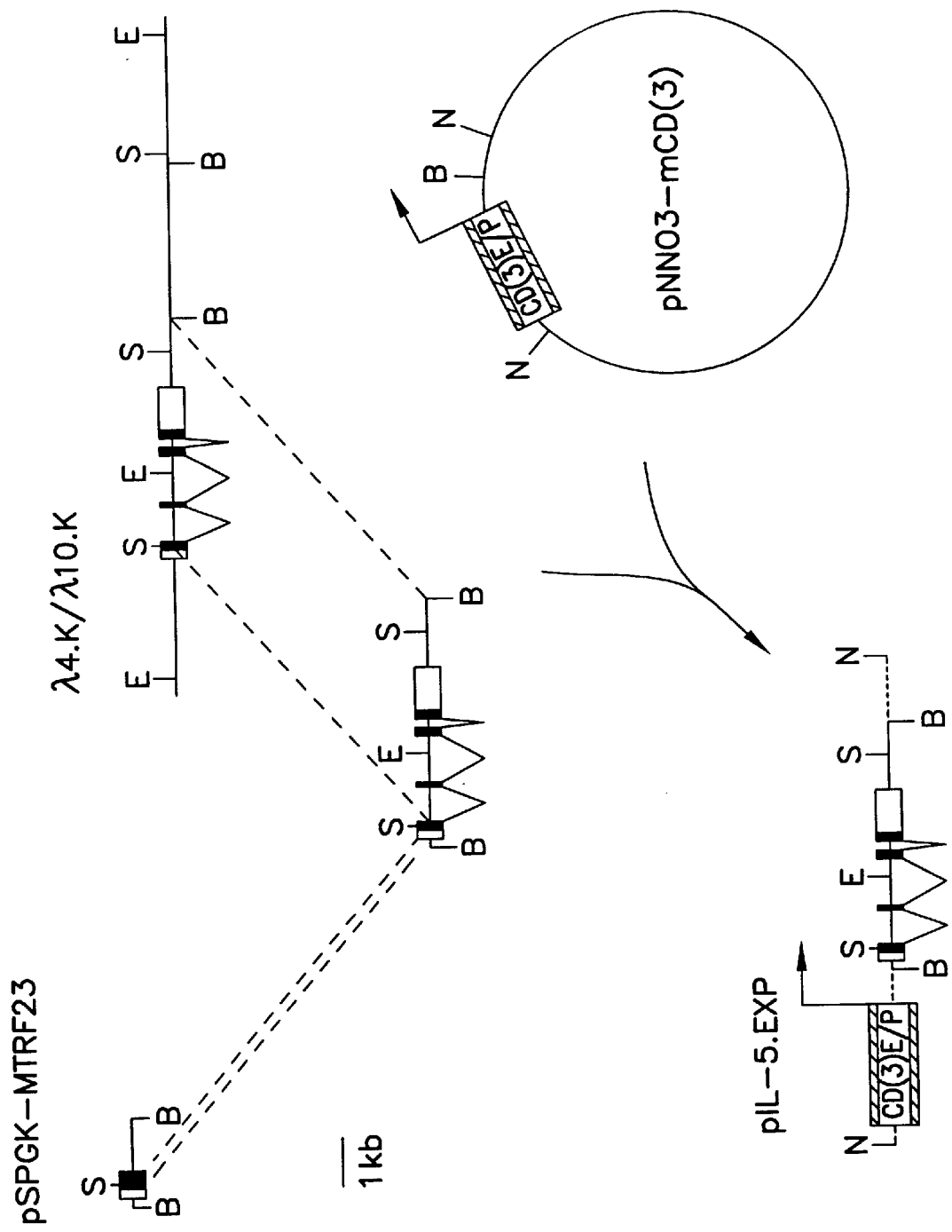
FIG. 1. Development of the IL-5 thymocyte/T cell transgene construct. The mini-gene construct was created as a cDNA:genomic fusion of sequences representing murine IL-5. Thymocyte/T cell specific expression of this fusion gene was achieved utilizing the basal promoter and tissue-specific enhancer (SEQ ID NO:3) of the murine CD3δ gene. The completed construct was cloned into the transgenic shuttle vector pNNO3 and the 5.6 kb transgene insert was excised with Not I prior to introduction into fertilized eggs.

Transgenic animals which express a cytokine in a tissue and/or cell specific manner can be models for disease states associated with expression of that cytokine in those tissues or cells. For example, transgenic mice expressing IL-5 from lung specific transcription control sequences, e.g., promoters and/or enhancers expressed in Clara cells in the lung (CC10), can be useful as a model for diseases characterized by the presence of pulmonary eosinophilic infiltrations: asthma, pulmonary eosinophilia, Loffler's syndrome, eosinophilic pneumonia, pulmonary fibrosis, Wegener's granulomatosis, lymphoidrnatoid granulomatosis, eosinophilic granuloma of the lung, adult respiratory distress syndrome, and post-trauma pleural effusions which contain eosinophils or eosinophil containing pleural effusions associated with infections, such as tuberculosis (see Spry, In: *Eosinophils*, Oxford University Press, pp. 205–212 (1988)).

Moreover, transgenic mice expressing IL-5 from a thymocyte and/or T cell specific transcription control sequence, e.g.,CD2 and CD3δ, can be useful as a model for diseases that are associated with T cell expression of IL-5; bacterial infections, e.g., Actinomycetales, Enterobacteriaceae, Staphlococcal, and Streptococcal infections, fungal infections, e.g., Aspergillosis and fungal lung diseases, leukemias, e.g., eosinophilic leukemia, myeolcytic leukemia, myeloblastic leukemia, Hand-Schuller-Christian disease, Letterer-Siew disease, Omenn's syndrome, Well's syndrome, Kimura's disease, rheumatoid arthritis, Sjogren's syndrome, pulmonary eosinophilia, acute and chronic bronchitis, asthma, and the like (For an exhaustive list of these diseases, which are well known to the art, see Spry, In: *Eosinophils*, Oxford University Press, (1988)).

Furthermore, such transgenic animals can be employed as vehicles to test agents which are known to, or which may be useful to, reduce or inhibit the expression of IL-5 in vivo. Agents which inhibit eosinophil-associated pathologies and thus, which may act by inhibiting IL-5 production, are known to the art.

"Isolated cytokine nucleic acid" is RNA or DNA containing greater than 15, preferably 20 or more, sequential nucleotide bases that encode a cytokine, e.g., interleukin-5, or a variant fragment thereof having biological activity, that is complementary to the non-coding strand of the native cytokine RNA or DNA, or hybridizes to said RNA or DNA and remains stably bound under stringent conditions. Thus, the RNA or DNA is isolated in that it is free from at least one contaminating nucleic acid with which it is normally associated in the natural source of the nucleic acid and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of isolated interleukin-5 nucleic acid is RNA or DNA that encodes a biologically active interleukin-5 polypeptide sharing at least 90% sequence identity with the murine interleukin-5.

As used herein, the term "recombinant nucleic acid," i.e., "recombinant DNA" refers to a nucleic acid, i.e., to DNA that has been derived or isolated from any appropriate tissue source, that may be subsequently chemically altered in vitro, and later introduced into target host cells, such as cells derived from animal, plant, insect, yeast, fungal or bacterial sources. An example of recombinant DNA "derived" from a source, would be a DNA sequence that is identified as a useful fragment encoding a cytokine, or a fragment or variant thereof, and which is then chemically synthesized in essentially pure form. An example of such DNA "isolated" from a source would be a useful DNA sequence that is excised or removed from said source by chemical means, e.g, by the use of restriction endonucleases, so that it can be further manipulated, e.g., amplified, for use in the invention, by the methodology of genetic engineering.

Therefore, "recombinant DNA" includes completely synthetic DNA sequences, semi-synthetic DNA sequences, DNA sequences isolated from biological sources, and DNA sequences derived from introduced RNA, as well as mixtures thereof. Generally, the recombinant DNA sequence is not originally resident in the genome of the host target cell which is the recipient of the DNA, or it is resident in the genome but is not expressed, or not highly expressed in a cell-specific manner.

As used herein, "chimeric" means that a vector comprises DNA from at least two different species, or comprises DNA from the same species, which is linked or associated in a manner which does not occur in the "native" or wild type of the species.

The recombinant DNA sequence, used for transformation herein, may be circular or linear, double-stranded or single-stranded. Preferably, it is linear and double stranded DNA. Generally, the DNA sequence is in the form of chimeric DNA, such as plasmid DNA, that can also contain coding regions flanked by control sequences which promote the expression of the recombinant DNA present in the cells into which the DNA is introduced. For example, the recombinant DNA may itself comprise a promoter that is active in mammalian cells, or may utilize a promoter already present in the genome that is the target for the introduction of the recombinant DNA. Such promoters include the CMV promoter, as well as the SV40 late promoter and retroviral LTRs (long terminal repeat elements). A preferred embodiment of the invention includes promoters and/or enhancers which result in cell- or tissue-specific expression. Preferred thymocyte/T cell-specific transcription control sequences include, but are not limited to, CD3δ and CD2. Preferred lung specific transcription control sequences include, but are not limited to CC10 and SPC. Cell- and/or tissue-specific transcription control sequences are well known to the art. Aside from recombinant DNA sequences that serve as transcription units for the cytokine or portions thereof, a portion of the recombinant DNA may be untranscribed, serving a regulatory or a structural function.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is generally accomplished by ligation at convenient restriction sites. If such sites do not exist, the synthetic oligonucleotide adaptors or linkers are used in accord with conventional practice.

Aside from recombinant DNA sequences that serve as transcription units for a cytokine or portions thereof, a portion of the recombinant DNA may be untranscribed, serving a regulatory or a structural function.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the introduced DNA in the cell or its progeny.

The general methods for constructing recombinant DNA which can be introduced into target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

The recombinant DNA can be readily introduced into the target cells, i.e., totipotent cells such as fertilized eggs, by methods well known to the art. For example, see Cordell, U.S. Pat. No. 5,387,742, issued Feb. 7, 1995, which is incorporated by reference herein. Although defined primarily by reference to mice, the constructs described herein can be used to produce other non-human mammalian transgenic species, including, but not limited to, rats, hamsters, sheep, pigs, rabbits, gerbils, cats, dogs, bovines, primates and the like.

"Southern analysis" or "Southern blotting" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37–9.52 of Sambrook et al., supra.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as $^{32}P$, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, NY, 1989).

"Stringent conditions" are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS. These abbreviations are defined in Sambrook et al., supra.

The invention will be further described by reference to the following examples.

EXAMPLE I

Materials and Methods

Molecular Biology and the Generation of Transgenic Mice.

Murine IL-5 containing DNA fragments (Tohyama et al., *EMBO J.*, 9, 1823 (1990)) were cloned in the plasmid vector pBluescript-KS(+) (Stratagene, La Jolla, Calif.) or the transgenic plasmid shuttle vector $pNNO_3$ as part of the construction of the murine IL-5 cDNA:genomic fusion gene (SEQ ID NOS:4-5). This minigene, together with the transcriptional regulatory elements of the murine CD3δ gene (SEQ ID NO:3) were excised free of plasmid vector sequences using Not I and gel purified by electroelution onto dialysis membrane. The purified insert DNA was filtered using centrifuge microfiltration units (0.2 µM; Schleicher and Schuell, Keene, N.H.) prior to injection into fertilized eggs derived from a cross of $F_1$ (CBA/J X C57BL/6J) females and C57BL/6J males.

Transgenic positive founder animals were identified from Southern genomic blots of tail DNA using a $^{32}P$-labeled random primed IL-5 cDNA probe. Subsequent generations of mice were the result of backcross onto either C57BL/6J or $F_1$ (CBA/J X C57BL/6J) hybrid mice and identification of transgenic positive offspring was accomplished by genomic Southern blot analysis and an IL-5 transgene-specific PCR based assay. The primers employed in the PCR based assay were derived from the CD3δ regulatory sequences (sense primer) and sequences from the first exon of the IL-5 gene (anti-sense primer). Sense primer: 5' ACCCCACAC-CTAGCCCACTG 3' (SEQ ID NO:1); anti-sense primer: 5' TGGCAGTGGCCCAGACACAGC 3' (SEQ ID NO:2). The final PCR reaction conditions were: ~200 ng genomic tail DNA, 2 mM $MgCl_2$, 400 µM of each dNTP, 0.2 µM of each oligonucleotide primer, 1×PCR Buffer II (Perkin-Elmer, Foster City, Calif.), and 2.5 units of Taq polymerase (Boehringer Mannheim, Indianapolis, Ind.). The reactions were routinely carried out in a volume of 50 µl using the Gene Amp PCR System 9600 (Perkin-Elmer, Foster City, Calif.). The reaction program used consisted of an initial denaturation step of 94° C. for 5 minutes, followed by 30 cycles of the repeating series 94° C. for 1 minute, 55° C. for 1 minute, and 72° C. for 2 minutes. The reactions were completed with a 72° C. 10 minute extension period.

RNA Isolation and Northern Blot Analysis.

Total RNA was prepared from cell populations and tissues using a guanidine thiocyanate-acid phenol extraction protocol. The high RNase content of infiltrating eosinophils necessitated two modifications of this standard protocol to purify intact RNA: the reducing agent dithiotheritol (DTT; Sigma, St. Louis, Mo.) was added at very high concentrations (0.2–0.5 M) and the volume of lysis buffer relative to the mass of tissue homogenized was increased several fold. Total RNA (15 µg) from each source was fractionated by gel electrophoresis on a 1.2% agarose gel containing formaldehyde and transferred to GeneScreen (+) per the instructions of the manufacturer (NEN-Dupont, Boston, Mass.). The filter was pretreated for 2 hours at 45° C. in a solution containing 5×SET (1×SET is 0.15 M NaCl, 30 mM Tris-HCl pH 8.0, and 2 mM EDTA), 10×Modified-Denhardts and 50 mM phosphate buffer (1M phosphate buffer contains 69 g of sodium monobasic phosphate and 134 g of sodium dibasic phosphate per liter). Following pretreatment, this solution was discarded and the filter was prehybridized and hybridized under the stringent conditions described below.

Initially, the filter was incubated with gentle agitation at 45° C. for 2 hours in 50% deionized formamide (Boehringer Mannheim, Indianapolis, Ind.), 5×SET, 1×Modified-Denhardts, 20 mM phosphate buffer, 2% SDS, and 100 µg/ml sheared and denatured salmon sperm DNA (Sigma, St. Louis, Mo.). This prehybridization buffer was subsequently discarded and the filter hybridized overnight at 45° C. in fresh buffer containing 3–5 ng/ml of a $^{32}$P-labeled random primed probe. The hybridized filter was washed as follows: the filter was rinsed several times with 4×SSC-1% SDS at room temperature and then washed at 65° C., first for 2×20 minutes in 4×SSC-1% SDS, then for 2×20 minutes in 1×SSC-0.2% SDS, and finally for 2×20 minutes in 0.1× SSC-0.2% SDS. Hybridization was visualized by autoradiography using Kodak XAR-5 x-ray film (Eastman Kodak, Rochester, N.Y.).

Serum IL-5 ELISA.

Peripheral blood (300–500 mm$^3$) was recovered by nicking the tail artery. Blood was collected in a 1.5 ml microcentrifuge tube and allowed to clot without agitation at room temperature for 30 minutes. The clotted blood was centrifuged at ~1000 rpm for 10 minutes at 4° C. to recover serum which was then frozen on dry ice and stored at −80° C. until use. IL-5 levels were measured in these serum samples using a murine-specific IL-5 ELISA kit from Endogen, Inc. (Boston, Mass.). Measurements were made either on direct serum samples or serum diluted with the diluent provided by the manufacturer. Calorimetric assays associated with this ELISA were performed using a Molecular Devices V max microplate reader.

Fluorescence Activated Cell Scanning (FACS) Analysis.

Peripheral blood (50–100 µl) was collected from the tail and diluted directly into 4 ml of 1×PBS. Cells were collected by centrifugation at 1000 rpm for 5 minutes at 4° C. and red blood cells (RBC) were removed by resuspending the cell pellets in 0.5 ml of RBC lysis buffer (0.15 M ammonium chloride, 10 mM potassium bicarbonate, 0.1 mM EDTA) and incubating for 5 minutes at 4° C. The lysed samples were diluted with 4 ml of 1×PBS containing 1% BSA and 0.1% sodium azide (PBS/BA) and white blood cells (WBC) were collected by low speed centrifiugation as described above. The WBC pellets were cleared of remaining cellular debris by an additional cycle of resuspension in 4 ml of PBS/BA followed by low speed centrifugation. This WBC pellet was resuspended in 0.1 ml of 1×PBS containing 0.1% sodium azide (PBS/A) and lymphocytes were stained by incubating for 20 minutes with anti-CD3ε conjugated with fluoresceine isothiocyanate (FITC), anti-CD45R (B220) conjugated with phycoerythrin (PE), and biotinylated anti-CD45. All antibodies were purchased from Pharmingen (San Diego, Calif.).

The stained cells were collected by low speed centrifugation and unbound antibody was removed by a single cycle of resuspension in 4 ml of PBS/BA and low speed centrifugation. The cells were resuspended in 0.1 ml of PBS/BA and stained for 20 minutes with streptavidin-613 (Gibco-BRL, Bethesda, Md.) and unbound streptavidin was then removed by a single wash cycle with 4 ml of PBS/BA. The final cell pellet was resuspended in 0.5 ml of 1×PBS containing 1% formaldehyde and 0.1% sodium azide and stored at 4° C. until FACS analysis. Flow cytometry was performed using a FACSvantage cytometer and CELLQuest software (Becton-Dickinson). Lymphocytes were identified as CD45 positive cells in a gated population based on forward and side scatter profiles. The fractions of this population that were CD3ε positive (T cells) or CD45R positive (B cells) were determined from sample analyses in which a minimum of 15,000 cells were acquired.

Tissue Histology.

Experimental animals were sacrificed by lethal injection or $CO_2$ asphyxiation prior to organ/tissue harvest. Biopsies for histology were fixed overnight in 10% phosphate-buffered formalin at room temperature. The fixed tissue samples were subsequently carried through an ascending ethanol series before equilibration in xylene and paraffin impregnation. Paraffin sections (6 µM) were stained with hematoxylin and eosin and photomicrography was accomplished with a Ziess Axiophot microscope using Kodak Ectochrome 100 film (Eastman Kodak, Rochester, N.Y.).

EXAMPLE II

T Cell Specific Expression of IL-5

Constitutive expression of IL-5 in a peripheral lymphocyte population was achieved with a cDNA:genomic IL-5 fusion gene using the murine CD3δ promoter and enhancer (FIG. 1). This IL-5 transgene was designed to mimic the systemic pattern of IL-5 gene activity (i.e., elevated peripheral lymphocyte expression) as determined from models of parasite infestation and clinical studies of allergic inflammation. The transgene construct directs peripheral T cell expression, uncoupled from factors that mediate endogenous IL-5 gene activity, as a consequence of two structural features.

The transgene construct was made by fusing in-frame a 170 bp fragment derived from the IL-5 cDNA (SEQ ID NO:4) with the remaining portion of the genomic IL-5 gene. Since the point of fusion was in exon 1, this hybrid gene (SEQ ID NO:5) has no upstream flanking sequences but includes all of the introns of the IL-5 gene as well as ~1.2 kb of 3'-flanking sequences. The transgene is thus devoid of all the known endogenous regulatory elements associated with IL-5 expression (Bourke et al., *Blood*, 85, 2069 (1995)) while retaining all of the structural features and sequences of the genomic IL-5 gene.

Peripheral T cell expression of this construct results from the use of regulatory elements derived from the murine CD3δ gene. CD3δ is a T cell specific cell surface protein that is part of the T cell receptor (TCR) complex and is involved in signaling mediated by major histocompatibility complex-TCR interactions. Expression studies of the CD3δ gene in both mice and humans have shown that this gene is activated during thymocyte maturation and continues to be expressed in all peripheral T cells. Hypersensitivity experiments and cell transfection studies showed that this pattern of expression was the result of an enhancer activity associated with an approximately 300 bp sequence in the flanking region downstream of the CD3δ gene. The utility of this enhancer element to drive peripheral T cell specific expression in transgenic mice has been demonstrated in studies which showed that by linking the CD3δ 3'-enhancer and the CD3δ basal promoter into one contiguous sequence, a regulatory element was created that is sufficient to drive expression of heterologous reporter genes in a temporal and spatial manner identical to the endogenous CD3δ gene. As a result, this IL-5 transgene construct promotes peripheral T cell expression of this cytokine, free from the influences of factors that regulate endogenous IL-5 expression.

EXAMPLE III

Generation and Characterization of Transgenic Mice Expressing IL-5 in Peripheral T Cells Several independent lines of transgenic mice were created using the CD3δ/IL-5 minigene construct. Three partially characterized lines of mice (NJ.759, NJ.1638, NJ.1643) were each found to contain integrations of 2–5 copies of this construct. In addition, individuals from each line of mice also exhibited a common set of phenotypic traits: dramatically elevated white blood cell (WBC) counts, peripheral blood eosinophilia (both in terms of eosinophil numbers and as a percentage of WBC), and the development of histopathologies that compromise the health and reproductive capabilities of these animals. To investigate further the pathophysiologic effects of peripheral expression of IL-5, one of these lines of mice (NJ.1638) was chosen for detailed study.

Figure 2A:
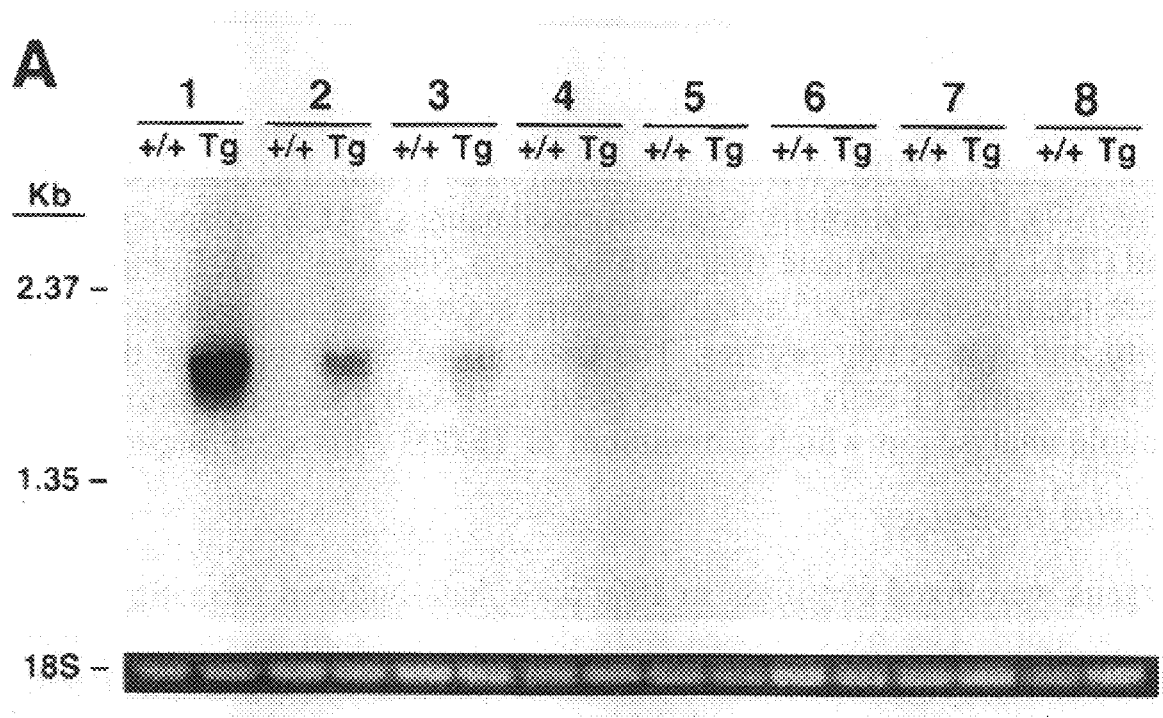
FIGS. 2A and 2B. Tissue-specific IL-5 gene expression and augmentation of IL-5 serum levels in transgenic mice. (A) Northern blot of wild-type C57BL/6J (+/+) and NJ.1638 transgenic (Tg) tissue RNAs probed with a random-primed $^{32}$P-labeled IL-5 cDNA. Each lane contains 15 μg of total RNA. Group 1, thymus; Group 2, bone marrow; Group 3, spleen; Group 4, lung; Group 5, leg muscle; Group 6, liver; Group 7, peritoneal cavity cells; Group 8, peripheral blood. A photograph of the 18S small ribosomal subunit stained with ethidium bromide is shown to verify the presence of RNA in each lane. (B) Quantitation of circulating serum protein levels using a murine-specific IL-5 specific capture ELISA. Serum IL-5 protein levels were assessed in wild-type mice at 7 months of age (+/+) and transgenic NJ.1638 mice at 1, 4, 7, and 10 months postpartum. Serum IL-5 levels were also measured in 7 month old mice infested with the helminthic parasite *Mesocestroides corti*. The *M. corti* tetrathyridia were maintained by serial passages in mice. Female C57BL/6J mice (>19 gms, Roswell Park Animal Resources) were intraperitoneally injected with 100 μl of packed tetrathyridiae obtained from long-term infested mice. Peripheral blood samples were taken for IL-5 serum protein determination ten days post infestation.

The tissue-specific expression of IL-5 in NJ.1638 mice was assessed by Northern blot analysis of total RNA derived from transgenic positive and age (7 months postpartum (p.p.)/sex (female)) matched normal (+/+) C57BL/6J mice (FIG. 2(A)). IL-5 transcripts were found in several of the NJ.1638 tissues examined. In particular, as predicted by the previous characterization of the CD3δ enhancer-promoter, IL-5 mRNAs were prevalent in the thymus. FIG. 2(A) also shows that IL-5 transcripts could be detected in peripheral sites known to contain sizable resident T cell populations (i.e., bone marrow, spleen, peritoneal cavity cells, lung, and blood). However, longer exposures of this blot showed that IL-5 transcripts can be detected even in tissues (i.e., liver and leg muscle) with only a small number of infiltrating T cells relative to the mass of tissue taken to make total RNA. Detectable steady-state levels of IL-5 mRNA were not found in any of the wild-type tissues examined.

Figure 2B:
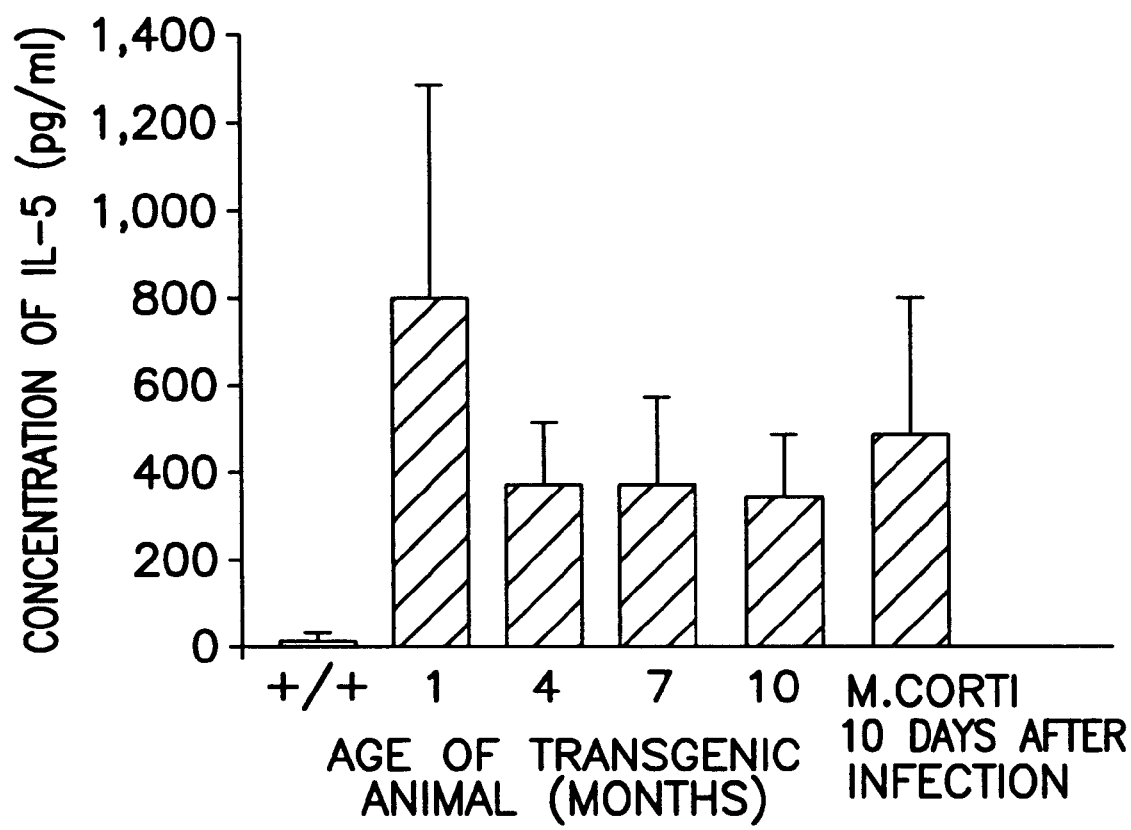

Circulating serum levels of IL-5 were measured in these transgenic mice as a function of postpartum age and the data are collected in the histograms contained in FIG. 2(B). A murine IL-5 specific ELISA (Endogen, Inc., Boston, Mass.) was used to measure serum IL-5 levels in transgenic, normal and parasite infested mice. IL-5 levels in the serum of wild-type (i.e., normal) animals were routinely at or below the level of detection of our assay ($\leq 2$–5 pg/ml of serum). The data shown in FIG. 2(B) represents wild-type animals at 7 months of age. Circulating IL-5 levels remain at this low level in wild-type animals regardless of the age of the animal examined.

Serum IL-5 levels in transgenic animals, however, quickly elevated to very high levels in postpartum mice (800 pg/ml in one month old animals) before dropping slightly to a steady-state serum level of approximately 400 pg/ml which was maintained throughout the life of the animal. The final histogram of FIG. 2B shows that the NJ.1638 steady-state serum IL-5 level was equal to the highest IL-5 levels found in wild-type mice infested with the helminthic parasite *M. corti* (10 days postinfestation).

EXAMPLE IV

Peripheral Eosinophilia and Other Alterations in Blood Leukocyte Populations

IL-5 overexpression in other characterized IL-5 transgenic mouse lines had previously shown that this cytokine induces a dramatic expansion of the number of blood eosinophils with only nominal effects on other mature leukocyte cell types (Tominaga et al., *J. Exp. Med.*, 173, 424 (1991); Dent et al., *J. Exp. Med.*, 172, 1425 (1990)). Consequently, eosinophil numbers, as a percentage of WBC, rose in these mice to as high as 60%. In addition, these expansions were also accompanied by mild increases in total WBC counts (3- to 7-fold).

Figure 3A:
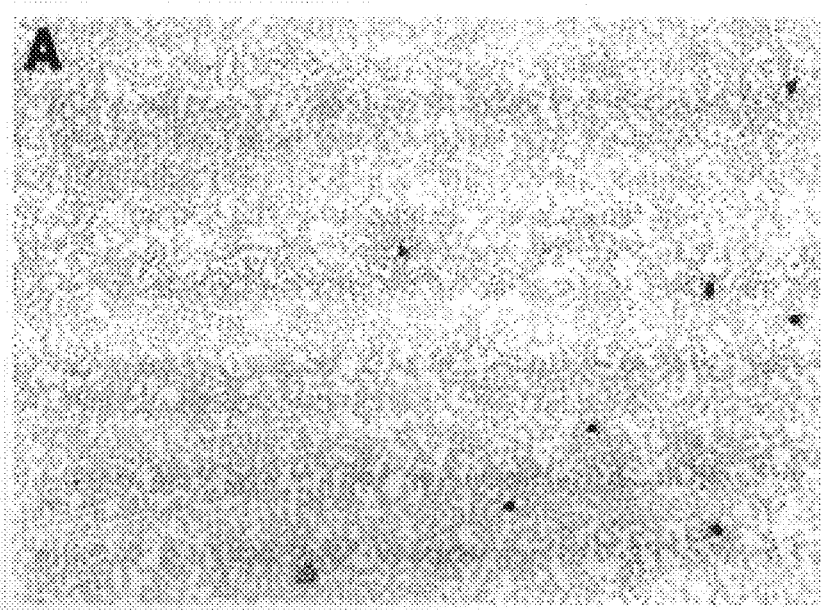
FIGS. 3A and 3B. Peripheral blood smears of 7 month old C57BL/6J (+/+) (A) and NJ.1638 transgenic (B) mice. Single-animal smear preparations were prepared from tail vein blood. The photographs shown are representative regions of equal cell density (i.e., equal red blood cell densities) stained with Wright-Giemsa.
Figure 3B:
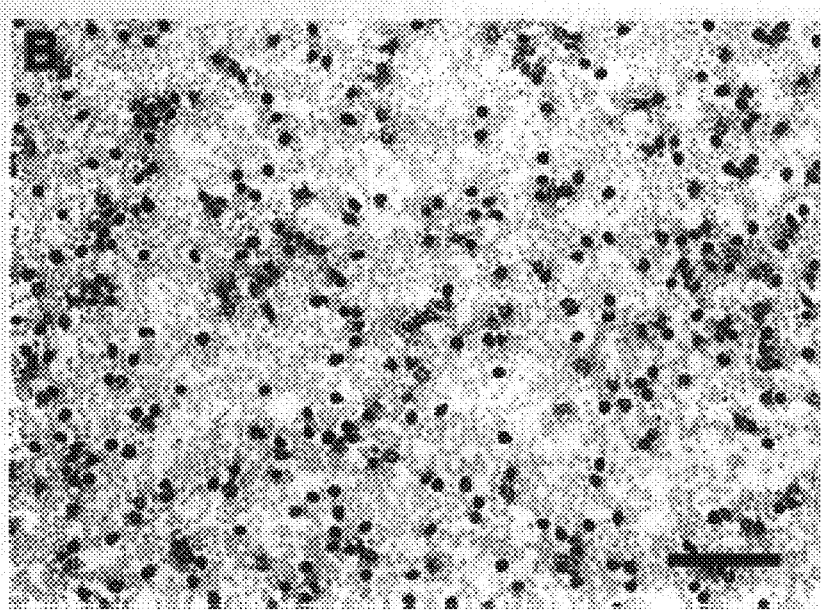

A similar phenomena was observed in NJ.1638 animals, although the effects of high-level peripheral IL-5 expression in these mice has far greater consequences than those observed in previous reports. FIG. 3 contains representative photographs of peripheral blood smears derived from wild-type and NJ.1638 mice. The transgenic mice suffered from both an obvious peripheral eosinophilia as well as a large increase in total WBC. The quantitative significance of these effects are shown in the blood differential data collected in Table 1.

TABLE 1

| age (months) | mouse | hematocrit | cell number/mm$^3$ of blood ($\times 10^{-3}$) | | | | |
|---|---|---|---|---|---|---|---|
| | | | total | lymphocyte | monocyte | eosinophil | neutrophil |
| 1 | +/+ | 47.6(0.6)$^5$ | 7.54(3.23)$^5$ | 6.00(3.00) | 0.80(0.34) | 0.07(0.08) | 0.67(0.29) |
| | NJ.1638 | 51.5(4.7)$^2$ | 55.23(12.54)$^4$ | 24.67(8.04) | 1.11(1.00) | 26.51(11.69) | 3.00(3.04) |
| 4 | +/+ | 52.0(2.9)$^7$ | 13.43(3.32)$^7$ | 10.88(2.98) | 0.56(0.35) | 0.42(0.32) | 1.55(0.40) |
| | NJ.1638 | 53.0(4.0)$^8$ | 86.20(33.08)$^8$ | 40.76(15.94) | 1.21(1.40) | 40.28(18.11) | 3.84(1.95) |
| 7 | +/+ | 43.7(2.5)$^3$ | 12.30(6.00)$^3$ | 9.43(5.3) | 0.80(0.72) | 0.37(0.25) | 1.70(1.08) |
| | NJ.1638 | 49.0(5.4)$^5$ | 245.80(180.54)$^4$ | 113.34(89.02) | 0.34(0.76) | 159.92(81.21) | 5.32(2.39) |
| 10 | +/+ | 48.9(3.8)$^9$ | 8.50(6.28)$^9$ | 6.43(4.46) | 0.62(0.43) | 0.10(0.10) | 1.36(1.55) |
| | NJ.1638 | 42.8(3.5)$^{10}$ | 331.64(250.82)$^8$ | 153.01(126.36) | 3.16(4.63) | 166.17(142.92) | 8.46(9.78) |
| 11 to 14 | +/+ | 44.8(1.9)$^5$ | 7.40(4.32)$^5$ | 5.68(3.33) | 0.32(0.16) | 0.34(0.32) | 1.02(0.68) |
| | NJ.1638 | 38.5(4.6)$^{26}$ | 390.67(261.92)$^{29}$ | 146.63(115.33) | 4.91(7.08) | 224.62(161.35) | 13.37(17.08) |
| 15 to 17 | +/+ | 43.8(1.8)$^5$ | 12.20(6.8)$^5$ | 9.68(6.93) | 0.84(0.37) | 0.30(0.21) | 1.42(0.31) |
| | NJ.1638 | 35.4(5.5)$^{16}$ | 476.88(269.46)$^{16}$ | 153.71(110.96) | 12.09(11.12) | 330.18(181.71) | 10.77(10.77) |

TABLE 1-continued

| age (months) | mouse | hematocrit | percentage of each cell type | | | |
|---|---|---|---|---|---|---|
| | | | lymphocyte | monocyte | eosinophil | neutrophil |
| 1 | +/+ | 47.6(0.6)[5] | 77.8(5.9) | 10.6(1.8) | 0.8(0.8) | 10.8(6.5) |
| | NJ.1638 | 51.5(4.7)[12] | 462.(15.4) | 2.0(1.8) | 46.8(13.8) | 5.2(4.4) |
| 4 | +/+ | 52.0(2.9)[7] | 80.6(5.1) | 4.4(2.9) | 3.0(2.0) | 12.0(3.5) |
| | NJ.1638 | 53.0(4.0)[8] | 47.5(7.4) | 1.4(1.4) | 46.2(6.4) | 4.8(2.2) |
| 7 | +/+ | 43.7(2.5)[3] | 73.6(17.4) | 5.6(2.9) | 4.2(4.7) | 16.7(14.0) |
| | NJ.1638 | 49.0(5.4)[5] | 45.1(4.2) | 0.4(0.9) | 50.7(6.5) | 3.7(3.5) |
| 10 | +/+ | 48.9(3.8)[9] | 76.6(9.0) | 8.0(3.7) | 1.8(2.3) | 13.4(7.0) |
| | NJ.1638 | 42.8(3.5)[10] | 46.3(12.1) | 0.7(0.8) | 50.0(11.2) | 2.9(1.9) |
| 11 to 14 | +/+ | 44.8(1.9)[5] | 76.2(4.5) | 4.6(2.0) | 4.0(1.3) | 14.3(5.0) |
| | NJ.1638 | 38.5(4.6)[26] | 37.5(14.0) | 1.7(2.7) | 56.9(14.6) | 3.8(3.7) |
| 15 to 17 | +/+ | 43.8(1.8)[5] | 73.8(12.6) | 9.2(6.1) | 2.3(1.0) | 14.8(7.7) |
| | NJ.1638 | 35.4(5.5)[16] | 30.4(14.6) | 2.8(2.2) | 64.1(12.9) | 2.7(2.5) |

Table 1. Peripheral blood cell counts and differentials as a function of postpartum age. Values appearing as exponents represent the number of measurements (i.e., animals) used to generate the data listed in the table. The tabular values in parentheses are the standard deviations associated with the measured numbers listed.

The total WBC counts and cell differentials included in this Table are derived from wild-type and NJ.1638 transgenic animals at different postpartum ages. The generation of CD3δ positive peripheral T cells in the mouse begins late in gestation approximately 17.5 days post coitum. As a result, elevated IL-5 expression begins prior to birth and the hematological consequences of this expression should be evident early in postpartum age. As shown in Table 1, the onset of effects induced by peripheral expression of IL-5 occurred by one month of age resulting in total WBC counts of these animals >55,000 cells/mm$^3$ of blood (i.e., greater than a 7-fold increase over wild-type animals). The percentage of cells that are eosinophils in these animals also increased from a basal level of 1% to 47% of total WBC. Moreover, transgenic positive newborns of transgenic negative mothers had WBC cellularities >30,000 cells/mm$^3$ with a peripheral eosinophilia of 30%. As the transgenic mice got older, this remarkable deviation from the normal cellularity of wild-type animals continued to expand virtually unabatedly. The total cellularity of the blood increased so that by 15 months of age NJ.1638 animals had an average peripheral WBC count greater than 40-fold over wild-type (476,880 cells/mm$^3$ of blood). Eosinophil levels in these mice also increased to 64% of total WBC (i.e., >300,000 eosinophils/mm$^3$).

The percentage increase of eosinophils in NJ.1638 mice occurred at the expense of other leukocytes whose fraction of total WBC decreased in each mature cell type. This observation, however, is misleading if the dramatic increases in total cellularity were not also taken into account. For example, neutrophils decreased from 5.2% of total WBC in one month old transgenic animals to 2.7% in 15–17 month old mice. In addition, each of these transgenic neutrophil percentages were lower than the average neutrophil percentage exhibited by wild-type mice (13.9%). However, because of the enormity of the increase in total WBC associated with NJ.1638 animals, neutrophil counts in these mice actually went up throughout the life of the animals, increasing to 10,770 neutrophils/mm$^3$ of blood (15–17 months) or >10-fold over wild-type levels. Similar observations were made for all of the non-eosinophil cell populations examined. In each case, the percentage of a given cell type decreases relative to wild-type mice, but in absolute terms peripheral expression of IL-5 at high levels resulted in massive increases in the total number of each of these peripheral blood cell types.

Table 1 also shows that hematocrits derived from both wild-type and NJ.1638 animals remained virtually unchanged. As a result, despite the dramatic increase of total WBC in NJ.1638 mice, red blood cells levels appeared not to be effected. However, whereas the hematocrits (i.e., red blood cell counts) of wild-type mice remained constant throughout the lifetime of the animals, the hematocrits of the transgenic animals decreased marginally with time. This observation reflects either a generalized decrease in the health of these animals with age, or perhaps long-term effects of systemic IL-5 expression resulting in an age dependent change in erythropoiesis.

EXAMPLE V

Physiological Changes of the Spleen and Liver Are Associated With CD3δ Driven IL-5 Expression The elevated levels of IL-5 expression in NJ.1638 mice also appeared to have dramatic physiological effects on several organ systems. The most prominent of these effects occurs in organ systems that engage in extramedullary hematopoiesis during the life span of the mouse (e.g., spleen-adult hematopoiesis, liver-fetal hematopoiesis). In wild-type mice, the spleen is a small (~80 mg wet weight) lymphoid organ that acts as a reservoir for peripheral B and T cell populations as well as circulating leukocytes. However, the spleen is also an important source of hematopoietic stem cells and accounts for nearly 10% of the adult animal's total hematopoietic capabilities.

Figure 4A:
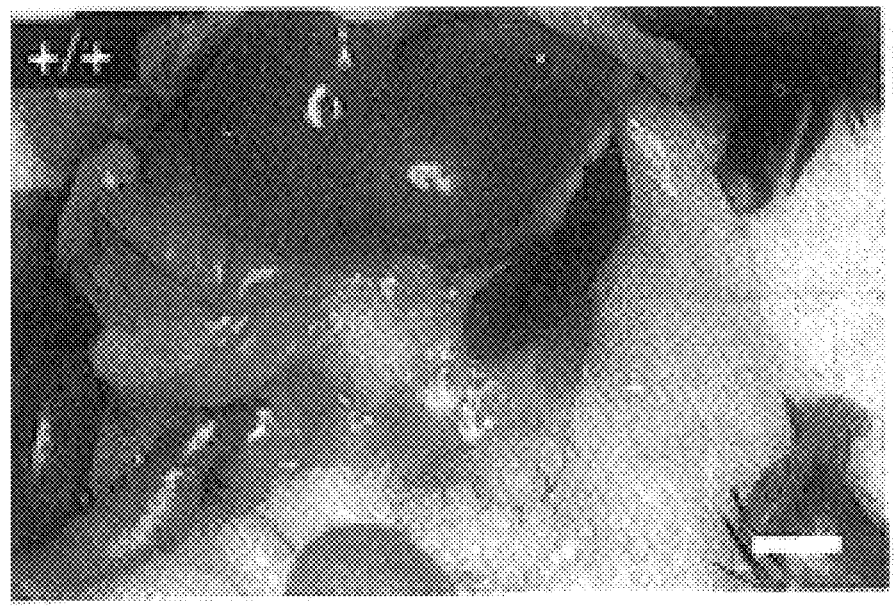
FIGS. 4A–4G. Perturbations in spleen and liver structure/cellularity resulting from constitutive high-level expression of IL-5 in thymocytes/T cells. (4A, 4B) Ventral view of the upper abdominal cavities of a 7 month old wild-type male (+/+) and an age and sex matched NJ.1638 mouse. The scale bar represents 0.5 cm. (4C) Assessment of splenomegaly in NJ.1638 mice as a function of postpartum age. Wild-type spleen weight (+/+) changed little in the time period examined. The wild-type spleen measurement shown are derived from animals 7 months of age. Spleen size is expressed as wet weight in mg. (4D, 4E) Hematoxylin and eosin (H/E) stained transverse sections through the spleen of a wild-type (+/+) and age matched NJ.1638 mouse. The solid bar in the lower right corner equals 62.5 μM. (4F, 4G) H/E stained transverse sections through the liver of a wild-type (+/+) and age matched NJ.1638 mouse. The scale bar in the lower right comer equals 125 μM.
Figure 4B:
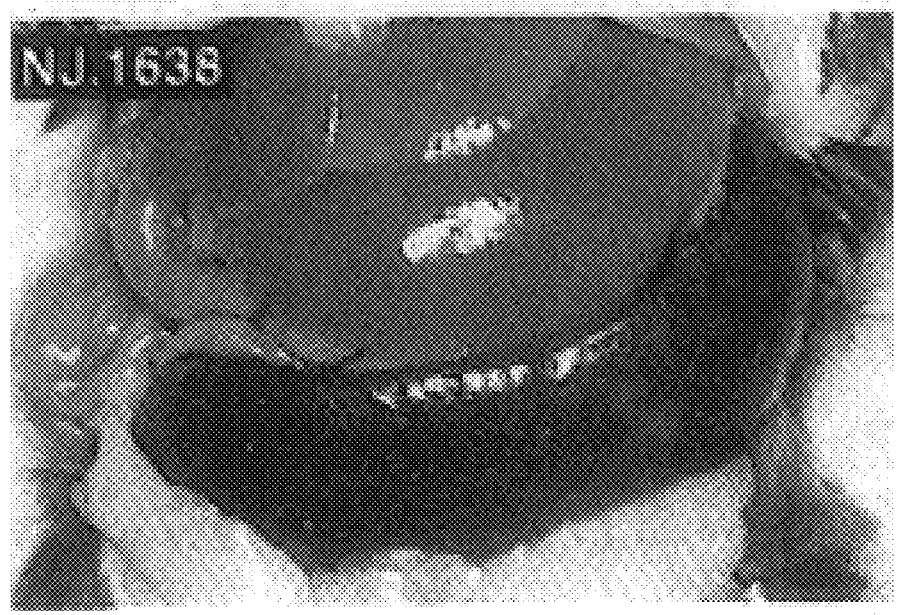
Figure 4C:
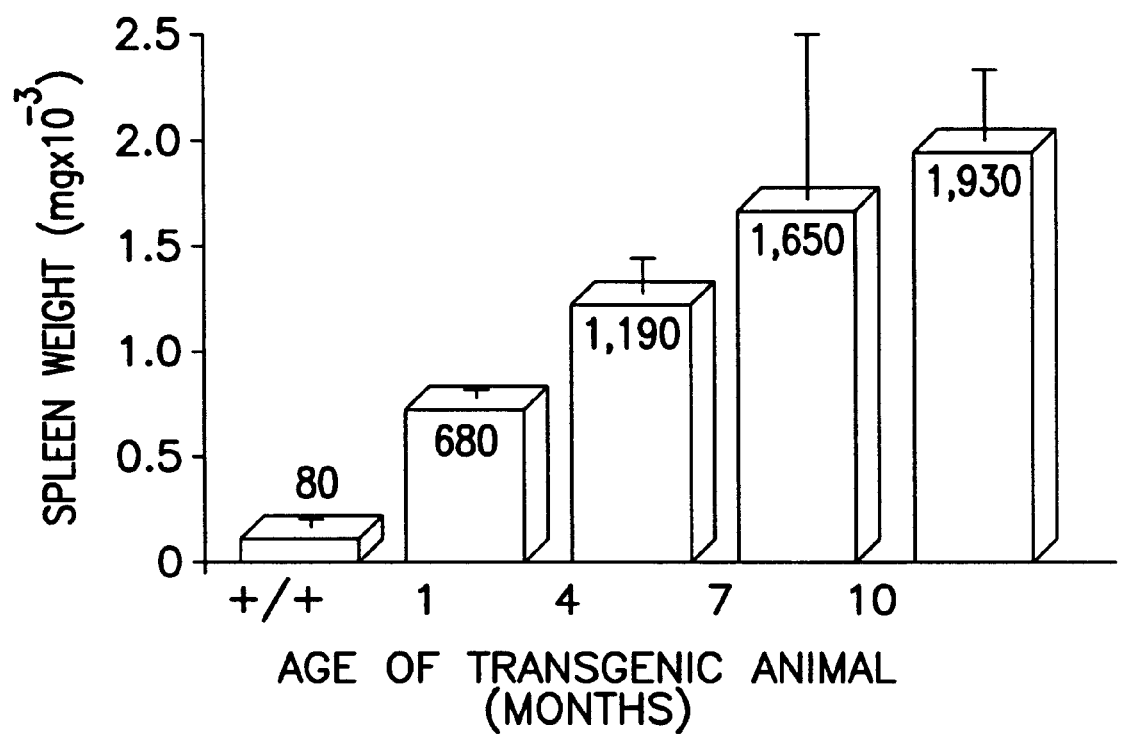

The effects of IL-5 expression on spleen size in NJ.1638 mice are dramatically illustrated in FIGS. 4A–4C. The photographs found in FIGS. 4A and 4B are ventral views of the upper abdominal cavity of a 7 month old wild-type mouse (+/+) in comparison to an age matched NJ.1638 mouse. Two effects on the spleen of transgenic mice were readily apparent. The spleen was enlarged in proportion to the expansion of the WBC counts of these animals. The wet weight of the transgenic spleen shown was 3.2 g (~40-fold increase over a wild-type spleen) and virtually filled the lower abdominal cavity.

A characterization of the splenomegaly that these mice suffer is shown in FIG. 4C. These data quantify spleen growth in NJ.1638 mice as a function of postpartum age. The kinetics of the observed splenomegaly is striking. The spleens of one month old animals were increased nearly 10-fold, averaging 680 mg in weight. The rate of expansion continued linearly with time throughout the life of the animal and as a result, by 10 months of age the average weight of a transgenic spleen was 1.93 g. To date, the largest of the spleen observed in an NJ.1638 mouse was a 5.28 g spleen (8 cm longitudinal axis) found in a 14 month old individual.

Figure 4D:
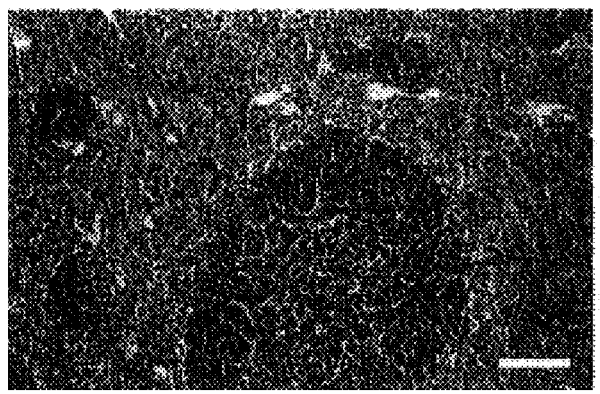
Figure 4E:
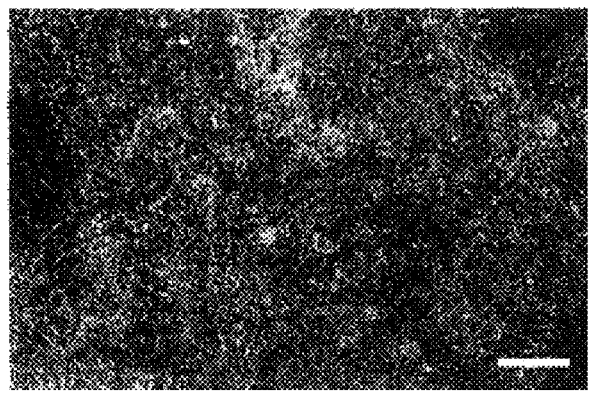

A closer examination of the transgenic spleen in FIG. 4(A) also revealed randomly distributed white patches or nodules suggesting the establishment of WBC foci and the exclusion of erythrocytes from these areas. The composition of these patches and the changes in transgenic spleen structure are shown in FIGS. 4D and 4E. FIGS. 4D and 4E contain photographs of hematoxylin-eosin (H-E) stained tissue sections from wild-type spleen (+/+) and transgenic spleen (NJ.1638). The homeostatic red/white pulp structure of the wild-type spleen was clearly evident and the overwhelming majority of WBC in this spleen were mononuclear lymphocytes. The structural integrity and cell composition, however, was completely abolished in the transgenic spleen. In addition to the loss of red/white pulp boundaries, mature eosinophils and myeloid progenitor cells comprised a substantial fraction of total splenocytes and were distributed throughout the spleen. The white patches visible on the transgenic spleen apparently represented large areas in the spleen containing exclusively leukocytes predominated by mature eosinophils.

Figure 4F:
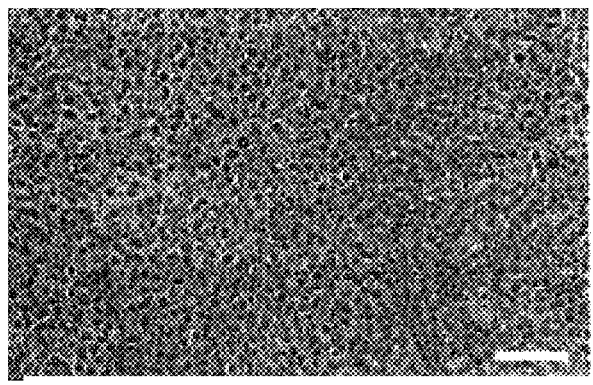
Figure 4G:
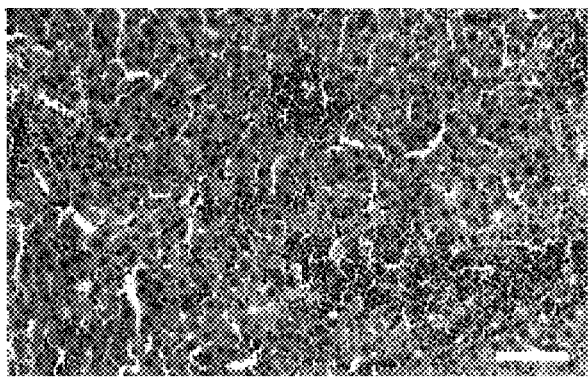

FIGS. 4A and 4B also demonstrate that by 7 months of age the liver of transgenic animals became enlarged as compared to wild-type (~2-fold increase). In addition, the transgenic livers also developed visible white patches which were shown to be concentrations of mature eosinophils and myeloid progenitor cells in the photographs of H/E stained sections of transgenic liver in FIGS. 4F and 4G. This panel includes photographs of wild-type (+/+) liver as well as transgenic liver (NJ.1638). The hepatic tissue of the transgenic animal became infiltrated with large numbers of myeloid cells (mostly mature eosinophils) with large foci of leukocytes surrounding the hepatic blood vessels. FIGS. 4F and 4G show that the degree of myeloid cell infiltration was substantial. Smear preparations of the liver cell suspensions also showed the presence of erythroblasts and maturing erythrocytes, demonstrating that IL-5 stimulation of the liver elicits a wide spectrum of hematopoietic activities.

EXAMPLE VI

IL-5 Induced Changes in Bone Marrow and Extramedullary Hematopoiesis

Cell differential analyses of the two prominent hematopoietic compartments in mice, the bone marrow and spleen were performed, to investigate the in vivo role of IL-5 in eosinophilopoiesis and to assess the other possible hematological effects of IL-5 over expression. These data are collected in the Tables that are a part of FIG. 5(see FIGS. 5(A) and (C), the data of which is duplicated in Tables 2 and 3, respectively). The data contained in these Tables includes total cell counts per femur or spleen, respectively, and "low resolution" cell differentials assessing the relative percentages of mature WBC and erythrogenic blast cells. Data were collected from both wild-type and NJ.1638 mice at 1, 4, and 10 months of age.

Total peripheral WBC counts of NJ.1638 mice grew by 40-fold over wild-type mice during the time frame examined, yet the systemic expression of IL-5 in these mice had no effect on total bone marrow cellularity (FIG. 5(A)). Transgenic femoral cellularity remained approximately the same as age matched controls, each apparently increasing with age only as a reflection of femur size. The lack of increase in total cellularity, however, did not result from a constancy in the relative proportions of each hematopoietic cell type. Eosinophils and their committed progenitors increased from 3% of total marrow cells in wild-type mice to more that 70% of the transgenic bone marrow. These increases result at the expense of the other marrow cell-types, all of which decreased in relative proportion from their wild-type levels. The decrease in erythroblast cells was of particular physiological relevance.

FIG. 5(A) shows that transgenic femoral marrow loses 75% of its steady-state erythroblast cells which probably accounts for the lack of visible red color of the resected femurs. Since the hematocrits of transgenic animals were equal to wild-type values, the loss of red blood cell production from the marrow must be compensated for by extramedullary erythropoiesis. Although histological analyses of the liver suggested that this organ is now erythropoietic, this activity was small compared to the increased erythropoietic activity demonstrated in the spleen (FIG. 5(C)).

TABLE 2

| age (months) | mouse | total cell/femur ($\times 10^{-6}$) | Percentage marrow cell types | | | | Eosinophil lineage cells/femur ($\times 10^{-6}$) | | | |
|---|---|---|---|---|---|---|---|---|---|---|
| | | | erythroblast | mononuclear | eosinophil | neutrophil | Class I | Class II | Class III | Class IV |
| 1 | +/+ | 24.08(2.90)[4] | 35.50(17.59) | 29.33(15.37) | 3.38(1.60) | 31.33(8.81) | 0.08(0.05) | 0.09(0.04) | 0.39(0.22) | 0.35(0.23) |
| | NJ.1638 | 17.12(3.02)[6] | 9.17(1.72) | 8.50(3.07) | 70.50(7.87) | 1.83(4.51) | 0.20(0.13) | 0.69(0.37) | 3.50(1.45) | 7.98(2.08) |
| 4 | +/+ | 32.65(13.85)[3] | 39.66(8.14) | 25.34(8.13) | 2.75(1.31) | 31.74(8.31) | 0.12(0.06) | 0.08(0.03) | 0.34(0.14) | 0.42(0.24) |
| | NJ.1638 | 31.65(3.60)[4] | 8.02(4.99) | 11.41(4.49) | 66.18(6.59) | 14.39(5.16) | 0.61(0.09) | 1.45(0.45) | 6.08(0.73) | 13.05 (2.53) |
| 10 | +/+ | 43.97(6.79)[3] | 37.76(4.77) | 19.63(2.47) | 3.16(1.74) | 39.45(8.92) | 0.25(0.18) | 0.08(0.05) | 0.65(0.43) | |
| | NJ.1638 | 33.23(4.58)[4] | 6.03(4.17) | 9.33(2.33) | 71.75(9.16) | 12.89(3.78) | 0.53(0.16) | 1.05(0.52) | 5.55(3.14) | 17.30 (1.13) |

TABLE 3

| | | | Percentage spleen cell types | | | | Eosinophil lineage cells/femur (×10$^{-6}$) | | | |
|---|---|---|---|---|---|---|---|---|---|---|
| age (months) | mouse | total cells/ spleen(×10$^{-7}$) | erythroblast | mononuclear | eosinophil | neutrophil | Class I | Class II | Class III | Class IV |
| 1 | +/+ | 17.50(3.64)$^3$ | 21.17(6.81) | 72.83(8.04) | 0.33(0.29) | 5.67(1.04) | 0.01(0.01) | <0.01 | 0.02(0.02) | 0.03(0.03) |
|   | NJ.1638 | 97.40(7.20)$^4$ | 28.88(2.14) | 19.38(2.36) | 48.25(2.75) | 3.50(1.47) | 0.85(0.46) | 1.40(0.44) | 12.27(2.71) | 33.23(5.65) |
| 4 | +/+ | 18.63(4.05)$^3$ | 19.99(13.99) | 76.14(15.90) | 0.62(0.80) | 3.25(2.60) | 0.03(0.03) | 0.01(0.01) | 0.02(0.02) | 0.13(0.17) |
|   | NJ.1638 | 311.40(120.49)$^4$ | 16.98(7.49) | 27.38(10.78) | 51.31(8.09) | 4.26(4.69) | 2.25(1.29) | 8.56(5.02) | 56.18(24.17) | 92.69(28.51) |
| 10 | +/+ | 20.33(2.32)$^3$ | 14.50(7.37) | 80.17(8.52) | 0.33(0.29) | 4.83(1.53) | 0.01(0.01) | <0.01 | 0.01(0.01) | 0.05(0.04) |
|   | NJ.1638 | 387.67(118.00)$^3$ | 8.00(3.46) | 40.50(7.40) | 47.50(7.50) | 4.00(3.00) | 4.30(2.78) | 7.12(4.41) | 60.72(37.50) | 122.13(44.95) |

The Tables contained in FIG. 5(C) show that the increased poietic activity was primarily a consequence of the dramatic increase in transgenic spleen cellularity. The cell differentials in the Table of FIG. 5(C) show the erythroblasts as a fraction of total spleen cells in one month old NJ.1638 mice were approximately equal to age matched wild-type individuals and the transgenic fractions actually decreased in comparison to wild-type spleens with the age of the animals. However, if the increase in spleen cellularity was taken into account, the erythropoietic capability of the transgenic spleen increased substantially over wild-type levels. For example, at 4 months of age erythroblasts represented 17% of splenocytes in transgenic mice as compared to 20% in wild-type mice. Since the total cellularity of the 4 month old transgenic spleen is $3.11 \times 10^9$ cells, as opposed to the $1.86 \times 10^8$ cells composing the wild-type spleen, the erythropoietic capability of the transgenic spleen has increased more than 14-fold $((3.11 \times 10^9) \times 17/(1.86 \times 10^8) \times 20)$.

The spleen cellularity data also demonstrated that unlike wild-type spleen which is composed of less than 1% eosinophils, these leukocytes become the predominant cell type of this organ as a result of IL-5 overexpression. Eosinophils represented approximately 50% of total splenocytes through the time frame examined and because by 4 months of age transgenic spleen cellularity was >$3 \times 10^9$ cells, the total number of eosinophils contained in the spleen of these animals was >$1 \times 10^9$ cells. These spleen eosinophils represented a reservoir greater than 16-fold the total number of eosinophils in peripheral circulation (e.g., at 4 months of age: $1.5 \times 10^9$ spleen eosinophils/($40.28 \times 10^3$ peripheral eosinophils/mm$^3$ of blood)$\times 2.2 \times 10^3$ mm$^3$ total blood volume). Although the proportions of other cell types in the transgenic spleen decreased relative to wild-type, the dramatic increase in total spleen cellularity resulted in similar increases in the total numbers of other WBC types stored in the transgenic spleen. These data probably reflect an immunological mechanism mediated by IL-5 in which preformed stores of these cells (particularly eosinophils) are generated and stored in the spleen for use as needed.

Liquid murine bone marrow cultures have shown that IL-5 uniquely induces the lineage-specific production of eosinophils. In contrast, two other cytokines associated with leukocyte production (IL-3 and GM-CSF) elicit the production of eosinophils as well as several leukocyte cell types (e.g., neutrophils and macrophages) in these in vitro cultures. However, IL-5 stimulation of IL-3 (or GM-CSF) treated bone marrow cultures will transiently produce eosinophils. These data suggest that IL-5 is a critical regulator of cells already committed to the eosinophil lineage, having only minimal effects on early granulocytic progenitor cell populations.

The in vivo data presented here and in previous transgenic mouse studies show that only IL-5 overexpression exclusively produces a massive increase in the number of mature eosinophils; i.e., a specific peripheral eosinophilia. These observations indicate that the homeostatic level of eosinophils in mammals is determined by several cytokine-receptor interactions, but that the production of elevated levels of these granulocytes in the face of parasitic infestation or allergic inflammation is controlled by IL-5 stimulation of a mitotically active eosinophil committed progenitor cell type.

To determine the validity of this conclusion, "eosinophil/eosinophil-progenitor" cell differentials were performed on bone marrow and spleen cells from wild-type and NJ.1638 transgenic animals. These data are converted into the absolute cell numbers contained in the Tables of FIG. 5(A) and (C) and are displayed in graphical form below each of these tables. Eosinophil differentiation was divided into four distinct stages termed "Class I, II, III, IV". This classification is based on nuclear morphology, Wright-Giemsa staining properties, and cytoplasmic granulation.

Class I cells ("promyelocytes") are characterized by a high nuclear to cytoplasmic ratio with spherical euchromatic nuclei. The cytoplasm of these cells have an intense basophilia and an absence of 1° (azuophilic) and 2° (specific) granules. Class I cells are mitotically active and committed to granulocytic differentiation, but not necessarily the eosinophil lineage.

Class II cells ("myelocytes") are the first cell type committed specifically to the eosinophil lineage. These cells are mitotically active, have a decreased nuclear to cytoplasmic ratio, and a nucleus undergoing morphological changes characterized by indention of the central region. The cytoplasm of these cells still retains a high degree of basophilia and contain small numbers of 1° granules.

Class III cells ("metamyelocytes") are the last mitotically active eosinophilic cell type prior to terminal differentiation. The nuclei of Class III cells are characterized by doughnut or ring shapes and the beginnings of condensation (i.e., a heterochromatic appearance). The cytoplasm of these cells is only slightly basophilic with evidence of both 1° and 2° granulation.

Class IV ("terminally differentiated eosinophils") is a quiescent cell type that initially resides in the marrow for several hours/days before exiting to the periphery. The nuclei of Class IV cells are heterochromatic and ring shaped, often twisting into "figure 8"-like structures. The cytoplasm of this cell type loses its basophilic staining properties and takes on the magenta coloration of the numerous and strongly eosin staining 2° granules. These terminally differentiated cells are the only class of cells that exit the marrow and, under homeostatic conditions, are the only eosinophil-like cell found in the periphery.

Figure 5B:
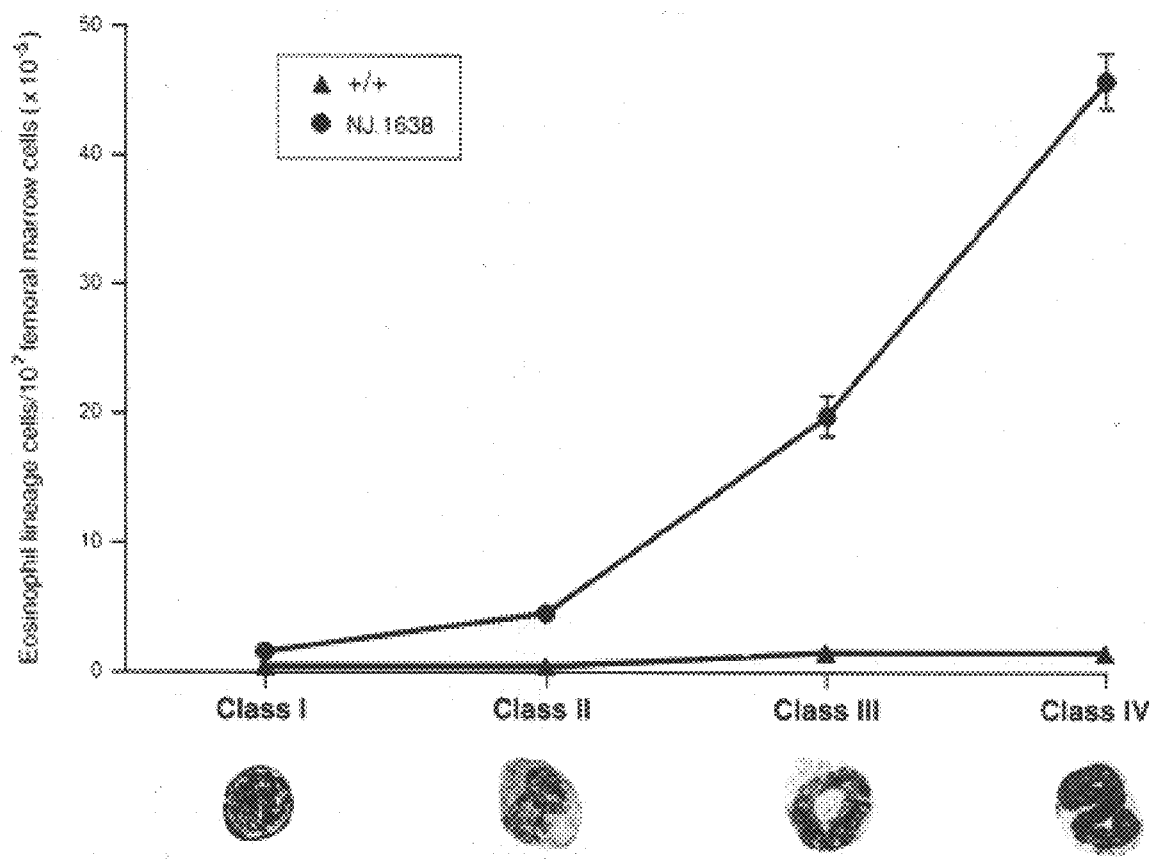
FIGS. 5A and B, C, and D. Cell differentials of bone marrow (A and B) and spleen (C and D) derived hematopoietic cells. Brush smear preparations of disassociated cells were stained with Wright-Giemsa prior to microscopy. The data from each tissue are presented in tabular form (A and C) and include total cellularity, individual progenitor and mature cell type percentages, and the absolute number of cells representing different stages of eosinophil differentiation. The tables provide data from wild-type (+/+) and NJ.1638 mice. Values appearing as exponents represent the number of measurements (i.e., animals) used to generate the data listed in the table. The table values in parentheses are the standard deviations associated with the measured and/or calculated numbers listed. *Mononuclear cell types include lymphocytes and monocytes/macrophages. ¶Only cells of the eosinophil lineage subtype class II, class III, and class IV were scored as marrow eosinophils. The description of the classes of cell types leading to and including mature eosinophils is found in the Detailed Description. †The number of cells in each class of eosinophil lineage cell type was calculated using the total cell counts and percentages listed in the tables as well as percentages derived from differentials of only eosinophil lineage cells: If £=the total number of eosinophil lineage cells (class I+class II+class III+class IV) then the total number of class I cells equals [£]×[percent class I cells derived from an eosinophil lineage differential]. Since the total number of (class II+class III+class IV) cells=[percent (%) tissue eosinophils]×[total WBC count], then £={[£]×[percent class I cells derived from eosinophil lineage differential]}+[percent (%) tissue eosinophils]× [total WBC count]. Therefore, £={[percent (%) tissue eosinophils]×[total WBC count]}÷{1−[percent class I cells derived from eosinophil lineage differential]}. The number of cells in each class of eosinophil lineage cell type was calculated by multiplying £ by the percentages of each cell type derived from the eosinophil lineage differentials. The graphs below each table represent histogram-like plots of the absolute numbers of cells in each eosinophil lineage class type/$10^6$ total tissue WBCs. The data presented represent average values of all age groups examined. The thumb print photographs are representative Wright-Giemsa stained cells of each granulocytic/eosinophil lineage class type.
Figure 5D:
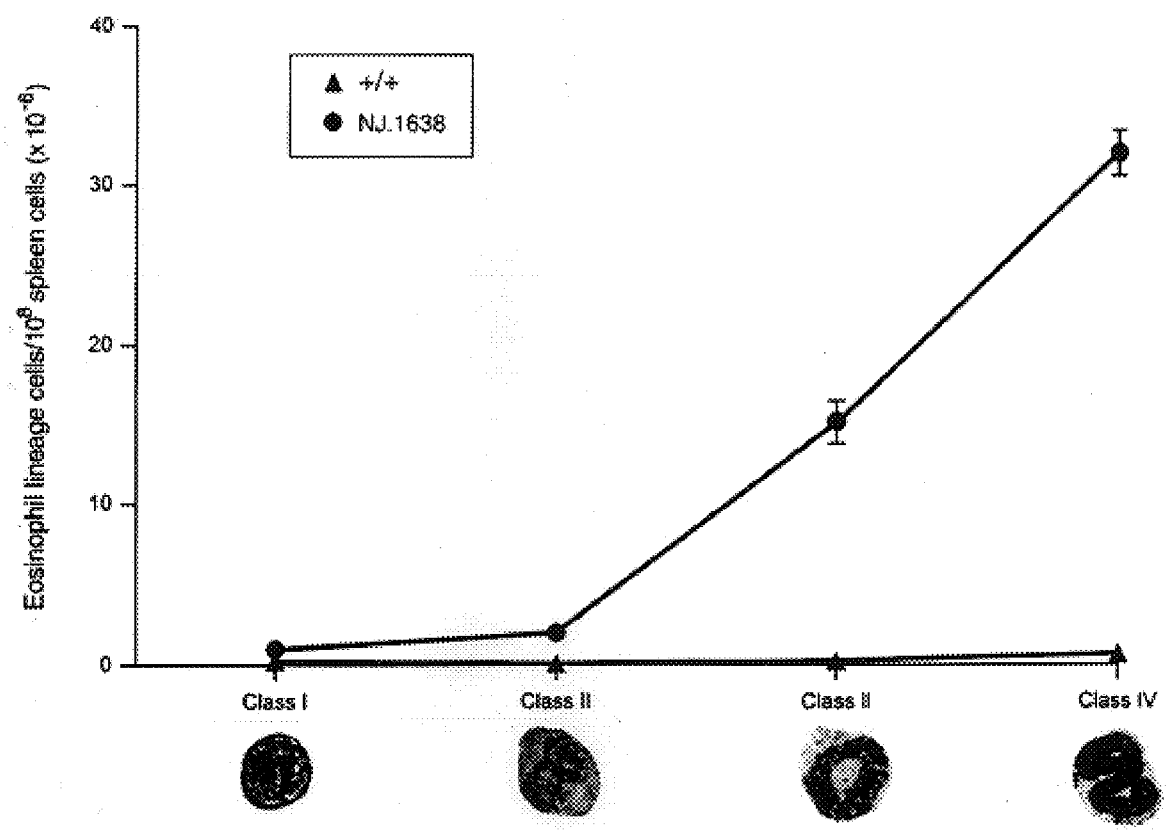

Thumb-print photographs of type examples for each eosinophilic class of cells are shown below the X-axes of the histograms in FIG. 5. The data displayed in the graphs of this Figure were an assessment of the IL-5 induced changes in the bone marrow (FIG. 5(B)) and extramedullary (FIG. 5(D)) eosinophilopoiesis. The absolute number of cells are plotted as a function of eosinophil class type. In wild-type mice, the numbers of mature eosinophils (Class IV) and progenitor cell types (Class I–III) represented a very small fraction (~3%) of total bone marrow cells and were nearly absent in the spleen (<1%). The graph of FIG. 5(B) shows that IL-5 stimulation of the bone marrow in NJ.1638 mice induced increases (compared to wild-type) in the number of cells representing each of the eosinophil lineage class types. However, the effects of IL-5 on more mature eosinophil cell types (Class III and IV) relative to the granulocytic cell type (Class I) and the earliest eosinophil lineage committed cell type (Class II) were substantial. The data show that IL-5 appeared to have specific mitogenic effects on more mature eosinophil lineage committed cells, increasing the number of cells representing Class III nearly 5-fold and Class IV >10-fold higher than Class II levels.

It is also important to note that the number of cells representing only eosinophil lineage committed Class types (II, III, IV) increased 10–30 fold relative to wild-type levels. This dramatic increase does not occur in the uncommitted granulocytic cell type, Class I. This specific stimulatory effect of IL-5 on more mature eosinophil committed cell types was also found in the extramedullary eosinophilopoiesis occurring in the spleen (FIG. 5(D)). Therefore, the original hypothesis of eosinophilopoiesis developed from liquid bone marrow cultures is essentially correct—interleukin-5 has substantive mitogenic effects only on more mature eosinophil committed cell types and is not the major regulator of the absolute numbers of early myeloid and granulocytic progenitor cell types.

EXAMPLE VII

Expression of IL-5 at High Levels Results in Eosinophilopoiesis at Extramedullary Sites The bone marrow total counts and cell differentials contained in the Table of FIG. 5(A) (duplicated in Table 2) show a large shift in hematopoietic activities toward the production of eosinophils. An examination of the total marrow cell numbers, however, demonstrated that this shift results in an eosinophilopoietic activity that was relatively minor compared to the extramedullary activity found in the spleen. For example, at 4 months of age the total number of eosinophilic progenitor cells (Class I, II, III) in the femoral marrow equals ~$1.63 \times 10^7$ cells (($0.61+1.45+6.08) \times 10^6$ cells/femur×2 femurs). In comparison, the spleen of the same animals contained greater than 40-fold more of these eosinophilic progenitor cells ($6.73 \times 10^8$ cells) suggesting that IL-5 is differentially stimulating extramedullary production of eosinophils.

The gene encoding the mouse eosinophil granule major basic protein (mMBP) is expressed in the bone marrow of wild-type mice and the prevalence of mMBP transcripts is unregulated in response to helminthic parasites. Measurable steady-state levels of mMBP mRNA were found only in tissue sites where eosinophilopoietic progenitor cell types were present; i.e., mature terminally differentiated eosinophils do not contain mRNAs coding for this 2° granule component. As a result, this assay is a sensitive method for the detection of early eosinophilic progenitor cells and thus tissue-specific eosinophilopoietic activities. The extent of these activities at different peripheral sites in wild-type and NJ.1638 mice is shown by the RNA gel blot analysis presented in FIG. 6.

Figure 6:
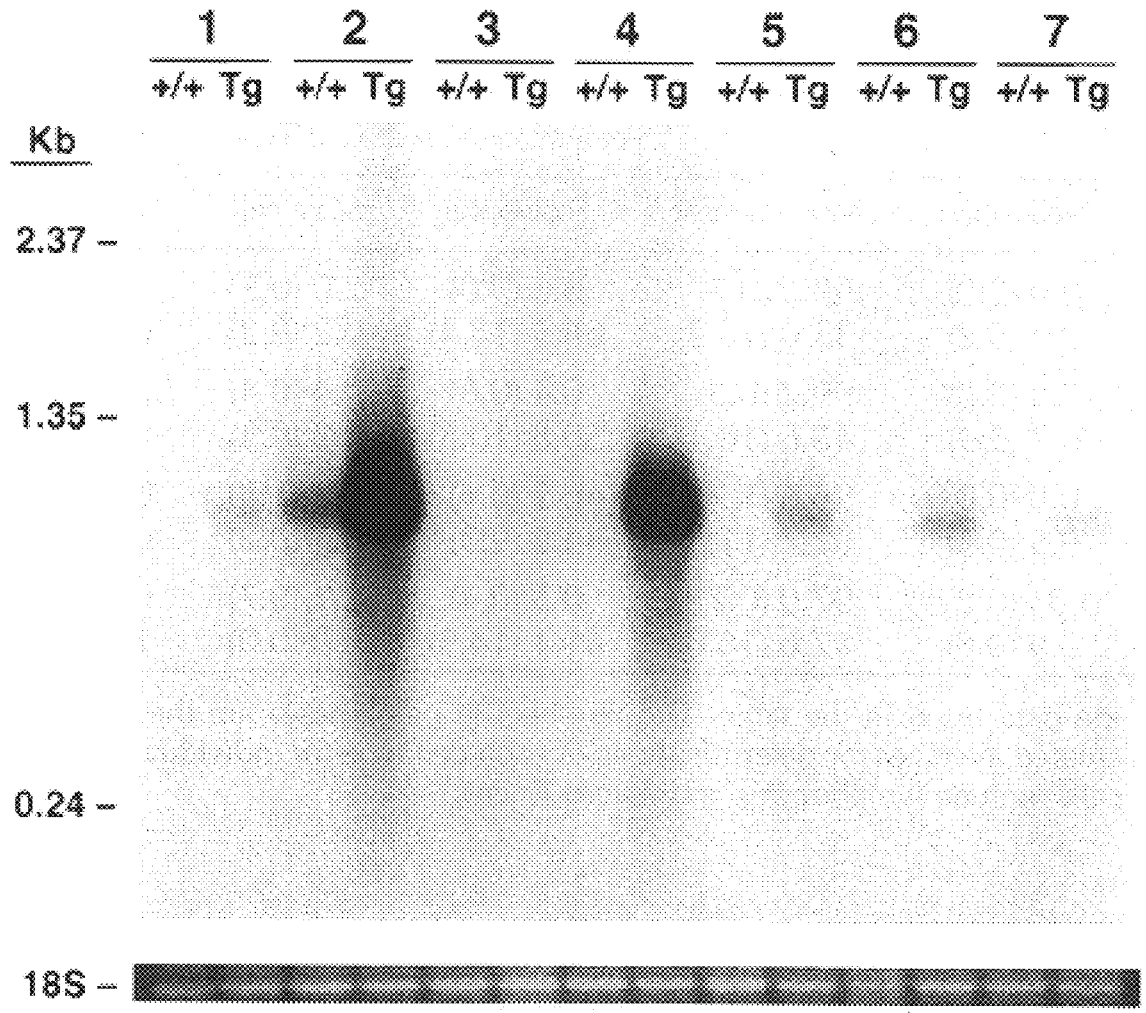
FIG. 6. Tissue-specific accumulation of eosinophil major basic protein (mMBP) gene transcripts. Northern blot of wild-type C57BL/6J (+/+) and NJ.1638 transgenic (Tg) tissue RNAs probed with a random-primed $^{32}$P-labeled mMBP genomic fragment, p9.35. Each lane contains 15 μg of total RNA. Group 1, peripheral blood; Group 2, bone marrow; Group 3, peritoneal cavity cells; Group 4, spleen; Group 5, liver; Group 6, lung; Group 7, leg muscle. A photograph of the 18S small ribosomal subunit stained with ethidium bromide is shown to verify the presence of RNA in each lane.

FIG. 6 contains a photograph of a Northern blot that includes total RNA from several tissues of 7 month old wild-type and age matched NJ.1638 mice. This blot was in agreement with histological analyses of mouse tissues which show that the only prominent location of eosinophilic progenitor cells in wild-type mice was the bone marrow. Longer exposures of this blot also showed the presence of small numbers of eosinophil progenitor cells in wild-type spleen. The lack of a hybridization signal in total RNA from transgenic peritoneal cavity cells, a compartment which lacks evidence of eosinophilic progenitors and whose cellularity is 50% mature eosinophils, demonstrated the specificity of this assay for only immature eosinophil lineage committed cells. These results confirm the bone marrow and spleen cell differential data shown in FIGS. 5(A) and (C), which showed that IL-5 stimulation causes the eosinophilic progenitor populations in each of these tissues to expand dramatically and this expansion is accurately reflected in the increase of tissue-specific MBP transcripts. The increase in spleen-derived transcripts was particularly dramatic owing to the tremendous increase in the number of eosinophil progenitor cells at this extramedullary site.

The data in FIG. 6 also demonstrated that IL-5 stimulation in vivo induces varying degrees of extramedullary eosinophilopoiesis (as judged by the presence of steady-state mMBP transcripts) in nearly all transgenic tissues examined. The overwhelming dominance of splenic extramedullary eosinophil production and the appearance of other peripheral focal clusters of eosinophilopoietic activity in NJ.1638 mice indicated that the fundamental mechanism by which IL-5 induces a rapid, and often massive, peripheral eosinophilia is probably through the establishment/elaboration of extramedullary sites of eosinophilopoiesis.

EXAMPLE VIII

A Massive Peritoneal Cavity Eosinophilia Accompanies CD3δ Driven IL-5 Expression Unlike wild-type mice, the peritoneal cavities of NJ.1638 mice were infiltrated by large numbers of cells, many of which were eosinophils. The peritoneal cavity cellularity of NJ.1638 mice as a function of postpartm age is shown by results presented in Table 4. Surprisingly, IL-5 expression in these mice resulted in a dramatic elevation in the total cellularity of the peritoneal compartment. This observation was correct even for young mice (one month of age). As shown in Table 4, the cellularity of this cavity in one month old mice increased to a level of >40-fold above numbers found in wild-type mice ($8.36 \times 10^7$ cells versus $1.96 \times 10^6$ cells). These extremely elevated levels (i.e., >$100 \times 10^6$ cells) persist as the animals get older although the kinetics of cell accumulation are somewhat complex (i.e., variable on a mouse to mouse basis).

The increases in cellularity found in these mice were also accompanied by a shift in cell composition. Whereas wild-type peritoneal cavity cells were composed of mostly mononuclear cells (lymphocytes and macrophage/monocytes) (~98%), the cells infiltrating the peritoneal cavity of NJ.1638 mice were generally 40–60% eosinophils and 40–60% mononuclear cells with a small (<1%) influx of neutrophils and mast cells (Table 4). This observation, together with the dramatic increases in peritoneal cavity cellularity, demonstrates that the large cellular infiltrate of this compartment is not simply the result of the influx of vascular eosinophils but is also the consequence of the specific recruitment of mononuclear cell types (10-fold increase over wild-type). In summary, the observations presented in Table 4 show that the peritoneal cavity cellularities of these transgenic mice are comparable in number and composition to the induced cellularity associated with helminthic parasite (*M. corti*) infestation of the peritoneal cavity and may reflect similarities in the mechanisms which induce each phenomena.

homeostatic resident population of eosinophils in wild-type mice. The advent of these "symptoms" appeared to be age dependent.

Several studies of large numbers of NJ.1638 animals (and age matched controls) are collected in Table 5. One of the more difficult issues associated with maintaining NJ.1638-derived mice was the sudden unexplained deaths that occur in these mice. The data found in Table 5 show that in a population of >100 NJ.1638 mice, 69% of these animals die

TABLE 4

| age (months) | mouse | cell number/peritoneal cavity (×10⁻⁶) | | | | percentage of each cell type | | | |
|---|---|---|---|---|---|---|---|---|---|
| | | total | mononuclear | eosinophil | mast cell | neutrophil | mononuclear | eosinophil | mast cell | neutrophil |
| 1 | +/+ | $1.96(0.11)^3$ | 1.92(0.10) | 0.00(0.00) | 0.04(0.01) | 0.00(0.00) | 98.00(0.69) | 0.00(0.00) | 2.00(0.69) | 0.00(0.00) |
| | NJ.1638 | $83.60(23.35)^3$ | 27.22(13.65) | 55.99(22.90) | 0.16(0.15) | 0.16(0.15) | 33.03(18.22) | 66.50(18.43) | 0.18(0.16) | 0.18(0.16) |
| 4 | +/+ | $7.30(3.30)^4$ | 7.24(3.28) | 0.02(0.03) | 0.03(0.04) | 0.00(0.00) | 99.20(0.49) | 0.35(0.57) | 0.40(0.40) | 0.05(0.1) |
| | NJ.1638 | $142.00(73.80)^3$ | 72.02(49.11) | 69.07(31.46) | 0.48(0.67) | 0.16(0.27) | 48.57(10.44) | 50.77(10.53) | 0.30(0.30) | 0.10(0.17) |
| 7 | +/+ | $6.43(2.12)^3$ | 6.21(2.01) | 0.02(0.04) | 0.17(0.11) | 0.00(0.01) | 96.76(1.73) | 0.23(0.40) | 2.63(1.82) | 0.10(0.17) |
| | NJ.1638 | $126.08(45.36)^6$ | 66.02(23.73) | 57.09(28.58) | 0.10(0.16) | 0.53(0.54) | 52.67(11.47) | 44.02(9.30) | 0.10(0.15) | 0.38(0.33) |
| 10 | +/+ | $7.92(2.21)^4$ | 7.68(2.16) | 0.05(0.05) | 0.16(0.07) | 0.03(0.02) | 96.98(0.69) | 0.50(0.44) | 2.08(0.70) | 0.43(0.34) |
| | NJ.1638 | $89.93(17.64)^3$ | 51.57(15.78) | 37.37(17.23) | 0.00(0.00) | 0.85(0.76) | 57.57(15.98) | 41.10(14.90) | 0.00(0.00) | 1.00(1.00) |

Table 4. Peritoneal cavity cell counts and differentials as a function of postpartum age. Values appearing as exponents represent the number of measurements (i.e., animals) used to generate the data listed in the table. The tabular values in parentheses are the standard deviations associated with the measured numbers listed.

EXAMPLE IX

Figure 7A:
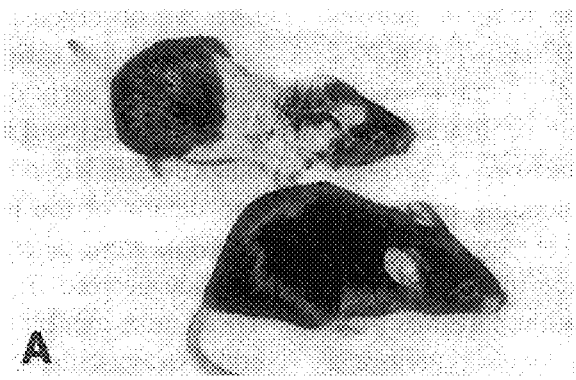
FIGS. 7A–7D. Histopathologies exhibited resulting from ectopic expression of IL-5 in NJ.1638 mice. All photographs shown were taken using Kodak Ektachrome 100 daylight slide film and a Nikon F3 camera. (A) Representative photograph of two NJ.1638 mice (14 months postpartum) exhibiting the extremes of dermal phenotypes found in these mice. (B) Higher magnification view of the mouse in panel (A) displaying hair loss and skin ulcerations. (C) Fully-body photograph of a 7 month old NJ.1638 mouse exhibiting spontaneous swelling of multiple peripheral lymph nodes. (D) Photograph of the genital-rectal areas of three NJ.1638 mice (14 months postpartum) showing either no pathology (mouse pictured on the far left) or different degrees of rectal prolapse.

CD3δ Driven Thymocyte/T Cell Production of IL-5 Results in a Variety of Inflammatory Histopathologies As noted above, three independent transgenic lines with the CD3δ/IL-5 construct were generated. Prior to the detailed analysis of individuals from the NJ.1638 line of mice, animals derived from all three founder mice had been observed to suffer from a series of inflammatory-like pathologies, including unexplained early death (average life expectancy of <12 months). The extreme severity of these pathologies in the founder NJ.759 and its offspring has led to the extinction of this transgenic line.

before 12 months of age (no deaths recorded in age matched wild-type mice). The death of many of these animals was not necessarily preceded by a deterioration of health. Postmortem examinations failed to unambiguously identify the cause of death, although in some of these mice the heart had enlarged 2-3-fold. Similar observations are seen in human HES (hypereosinophilic syndrome) patients and are consistent with other inflammatory diseases involving the expansion of eosinophil numbers. The most common of the overt histological pathologies experienced by these mice was the loss of hair and ulceration of the skin. Photographs of a mouse exhibiting typical dermatological lesions are shown in FIGS. 7(A) and (B).

TABLE 5

| Mouse | Age (months) | Histopathology | Total no. of animals | No. of animals exhibiting pathology | Frequency of occurrence (%) |
|---|---|---|---|---|---|
| Normal | 0–12 | Death by 12 months of age | 131 | 0 | 0% |
| NJ.1638 | 0–12 | | 102 | 70 | 69% |
| Normal | 0–6 | Loss of hair and development of ulcerating skin lesions | 40 | 0 | 0% |
| | 6–12 | | 40 | 0 | 0% |
| | >12 | | 40 | 0 | 0% |
| NJ.1638 | 0–6 | | 38 | 0 | 0% |
| | 6–12 | | 24 | 8 | 33% |
| | >12 | | 21 | 16 | 76% |
| Normal | 0–12 | Extreme congestion and swelling of lymph nodes | 131 | 0 | 0% |
| NJ.1638 | 0–12 | | 102 | 9 | 8.8% |
| Normal | >12 | Occurrence of rectal prolapse | 40 | 0 | 0% |
| NJ.1638 | >12 | | 21 | 3 | 14% |

Figure 7B:

To determine the scope and details of the histopathologies that result as a consequence of IL-5 overexpression in thymocytes/T cells, hundreds of mice derived from the NJ.1638 founder were systematically examined over 24 months. In addition to splenomegaly and liver pathologies (see FIGS. 4A–4C), these mice exhibited signs of immune-mediated inflammation at peripheral sites that have a high The two mice in panel (A) are NJ.1638 individuals that are 14 months of age. Whereas one of these mice exhibited the hair loss and skin ulceration sometimes found in NJ.1638 mice, its age matched transgenic littermate appeared healthy and showed no sign of dermatological problems. FIG. 7(B) shows a close-up view of the effected individual. Alopecia was a common occurrence in these mice and usually preceded skin ulceration.

Table 5 lists the dermatological observations associated with NJ.1638 mice as a function of postpartum age. In mice 0–6 months of age no incidents of dermatological problems were observed. However, in the next interval, 6–12 months of age, approximately one third of the animals examined showed evidence of hair loss and skin ulceration. In mice surviving >12 months of age, the frequency of skin pathologies increased to >75%. Once established, the number and severity of the skin lesions usually increased rapidly. These severely effected mice often became lethargic, showed signs of kyphosis, and had a high rate of mortality.

Figure 7C:
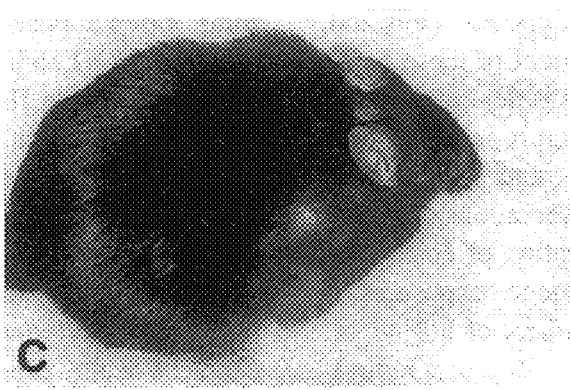

The spontaneous swelling of lymph nodes as the result of the accumulation of peripheral WBC was a recognizable phenotype of NJ.1638 mice. An example of this syndrome is shown in the photograph of FIG. 7(C). Several peripheral lymph nodes below the skin of the mouse in this photograph had enlarged as a result of the accumulation of cells. The lymph nodes enlarged as a solid mass characterized by the presence of several cell types. Although the identity of all of the cells composing these nodules had not been determined, many of the cells were mature eosinophils, non-eosinophil myeloid progenitor cells, and B/T lymphocytes. A quantitative assessment of the frequency with which this phenotype occurs is shown in Table 5. Enlarged lymph nodes occurred in nearly 9% of NJ.1638 mice below the age of 12 months. The frequency of occurrence did not appear to be an age dependent phenomena and spontaneously occurred with equal frequency in all age groups of mice studied. In addition, the enlargement of lymph nodes was not restricted to the periphery. Swelling and cell accumulation also occurred within the lymph nodes associated with the intestine (Peyer's patches) as well as the ventral mesenteric lymph nodes. These observations suggest that lymph nodes become congested with cells either because of IL-5 stimulated poietic activities similar to other extramedullary sites or IL-5 overexpression promotes the spontaneous occurrence (and/or enhances the survival) of leukemic/lymphomic transformations which proliferate in the nodes.

Figure 7D:
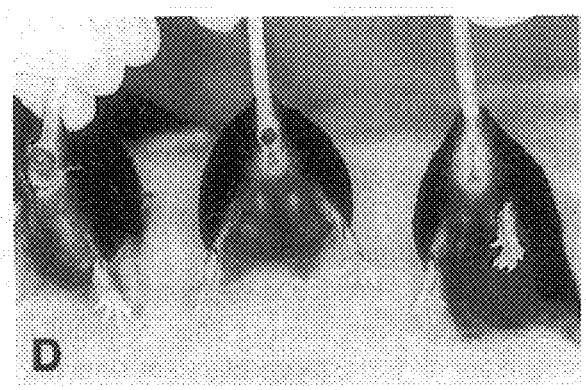

NJ.1638 mice also experienced inflammatory symptoms of the lower bowel exemplified by the occurrence of rectal prolapse. The occurrence of this pathology was strictly an age dependent phenomena and was found only in mice surviving >12 months of age. FIG. 7(D) contains a photograph of the genital-rectal area of three 14 months old NJ.1638 mice. These animals were selected because they show the spectrum of rectal pathologies that were found in these transgenic mice, including no rectal pathology (far right), minor rectal prolapse (middle), severe rectal prolapse with wet loosen stool (far left). Table 5 shows that the frequency with which rectal prolapse occurs in these older mice was 14% (rectal prolapse was not seen in any of the control animals in this study).

In general NJ.1638 mice are in poor health and have diminished reproductive capabilities relative to age and sex matched controls. These symptoms were so severe in another independently derived transgenic line (NJ.759) that it led to the extinction of this line.

This suggests that the observed pathologies occur secondarily as either a consequence of immune changes induced in the mice in an age dependent manner or occur as a result of an additional signal that elicits an uncontrolled inflammatory cascade. This additional signal may be as simple as a slight irritation and scratching. The induced physical trauma may elicit eosinophil degranulation and since the number of cells are so high, the resulting reaction quickly escalates into a severe pathology.

Figure 8:
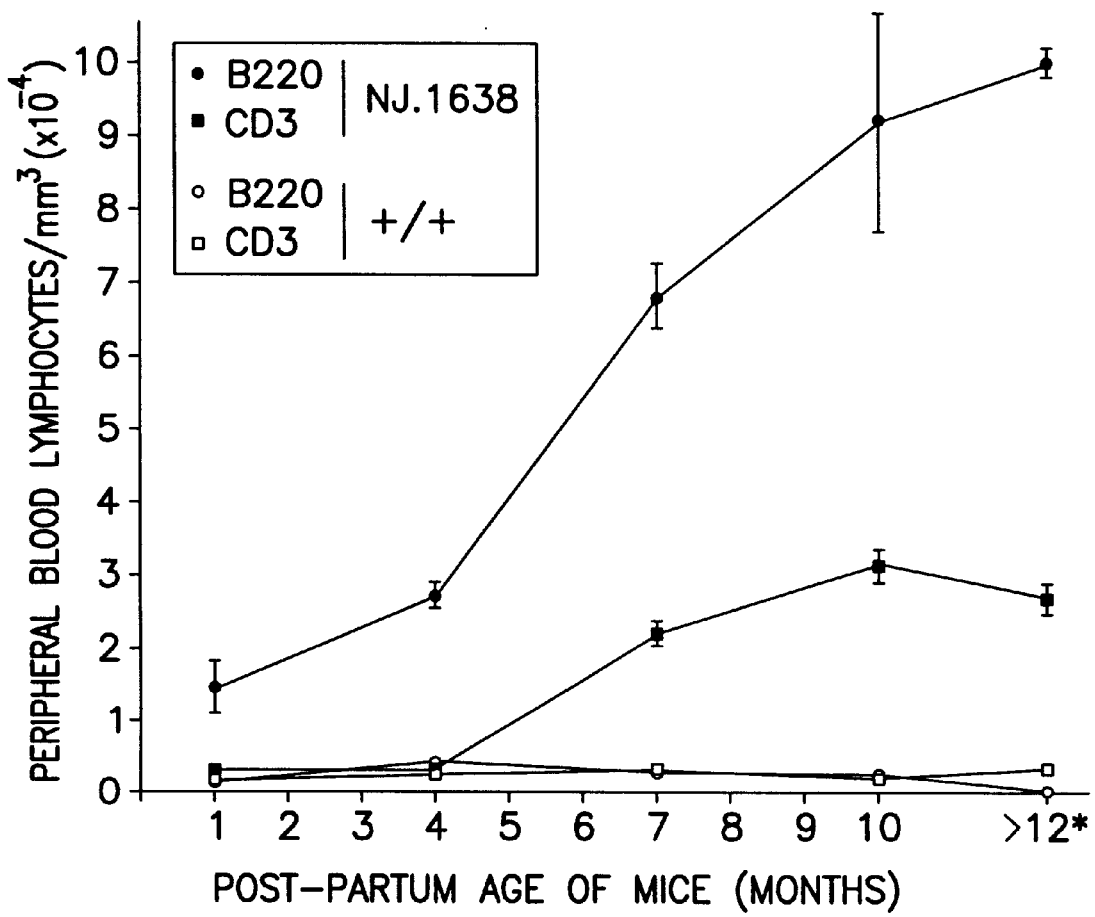
FIG. 8. IL-5 induced changes in NJ.1638 lymphocyte population kinetics as a function of postpartum age. Peripheral blood of NJ.1638 mice, and age matched wild-type controls, were analyzed by FACS using the T cell specific marker CD3 and the B cell marker B220. The data reduction was accomplished through the assessment of the fraction of cells identified by each marker relative to a lymphocyte gate established from scatter blots of total white blood cells (WBC). The data points shown were generated by multiplying the FACS-derived percentages by the absolute number of lymphocytes determined from cell differentials of peripheral blood (see Table 1). In all cases, the data points presented are the result of the analyses of multiple individuals (n≧4).
Figure 9:
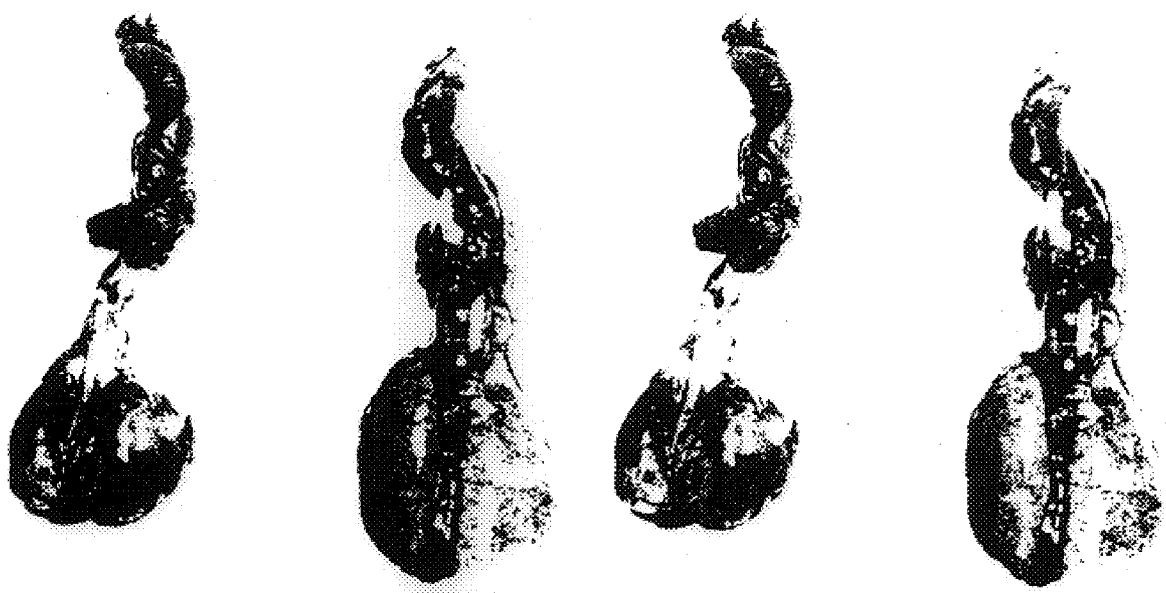
FIG. 9. Lungs dissected from wild-type (left) and CC10/IL-5 transgenic (right) mice.
Figures 10A, 10B:
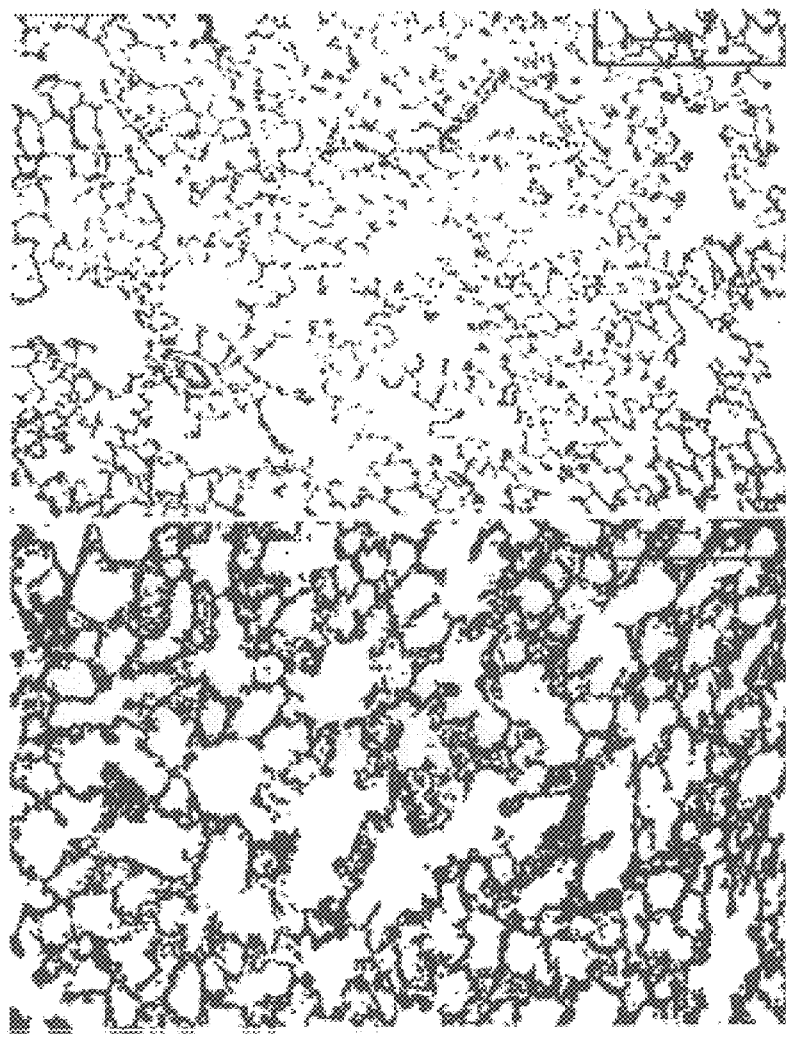
FIGS. 10A and 10B. Histological sections from the lungs of wild-type (A) and CC10/IL-5 transgenic (B) mice. The lungs of transgenic mice have gross distortions in the alveoli. Eosinophils are clearly present in the transgenic lungs.
Figures 11A, 11B:
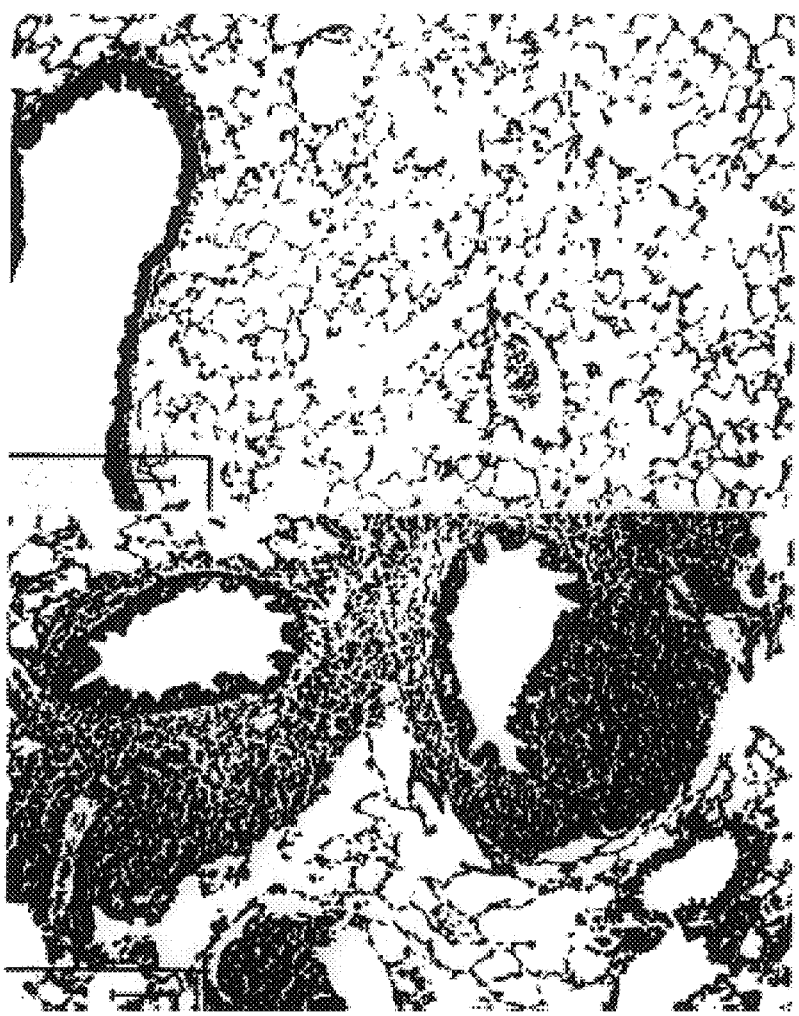
FIGS. 11A and 11B. Histological sections from the lungs of wild-type (A) and CC10/IL-5 transgenic (B) mice. These sections show the massive increase in cellularity in the peri-bronchial lymphoid tissues of the lung of transgenic mice.
Figures 12A, 12B, 12C:
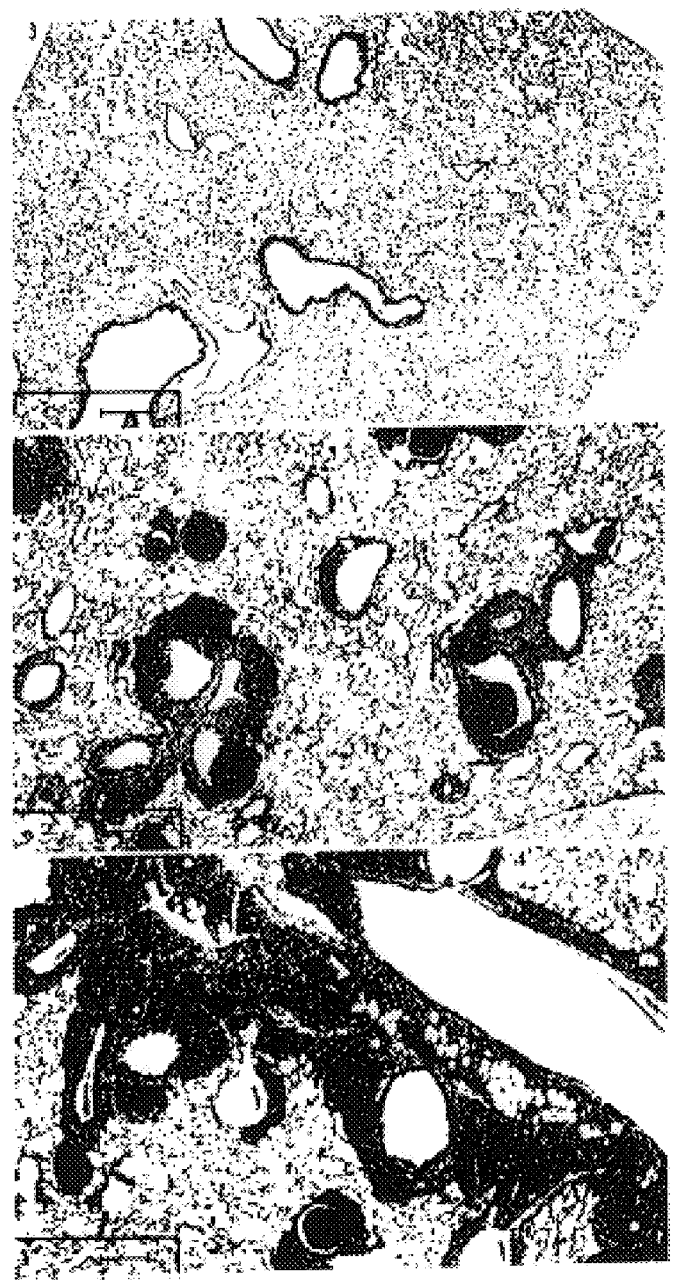
FIGS. 12A–12C. Histological sections from the lungs of wild-type (A) and CC10/IL-5 transgenic (B and C) mice. These sections show the massive increase in cellularity in the peri-bronchial lymphoid tissues of the lung of transgenic mice.
Figure 13A:
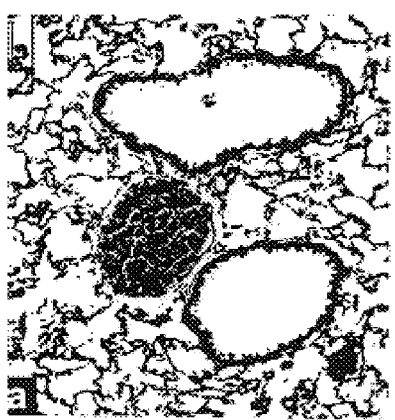
FIGS. 13A–13F. Immunofluorescence of the lung sections from a CD3δ.IL-5 (line 1638) transgenic mouse. These sections were stained with an eosinophil-specific antibody to the major basic protein (MBP) of the eosinophil granule. a) lung stained with H&E; b) lung stained with anti-MBP; c) negative control for background fluorescence; d) an enlarged lymph node from the intestine stained with H&E; e) an enlarged lymph node from the intestine stained with anti-MBP; f) negative control for background fluorescence.
Figure 13B:
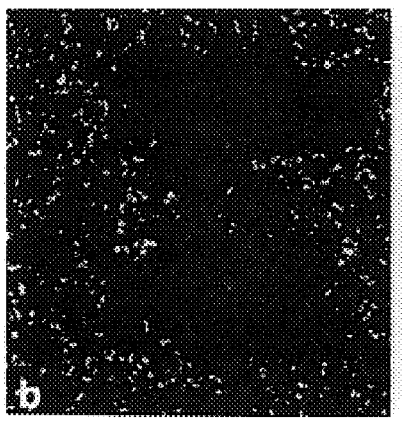
Figure 13C:
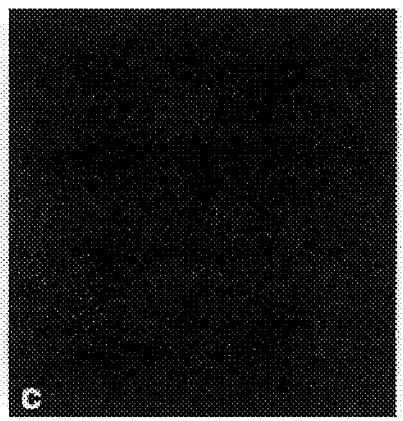
Figure 13D:
Figure 13E:
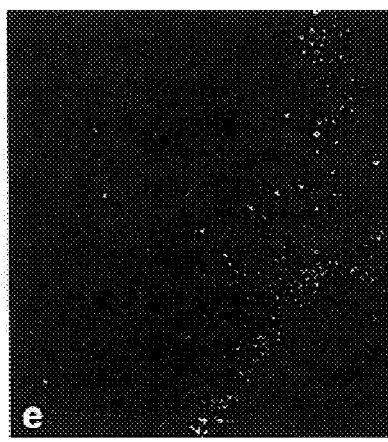
Figure 13F:
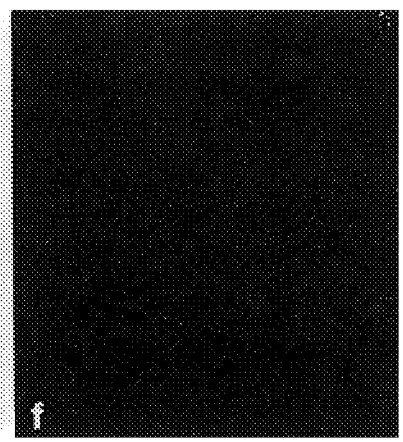
Figures 14A, 14B:
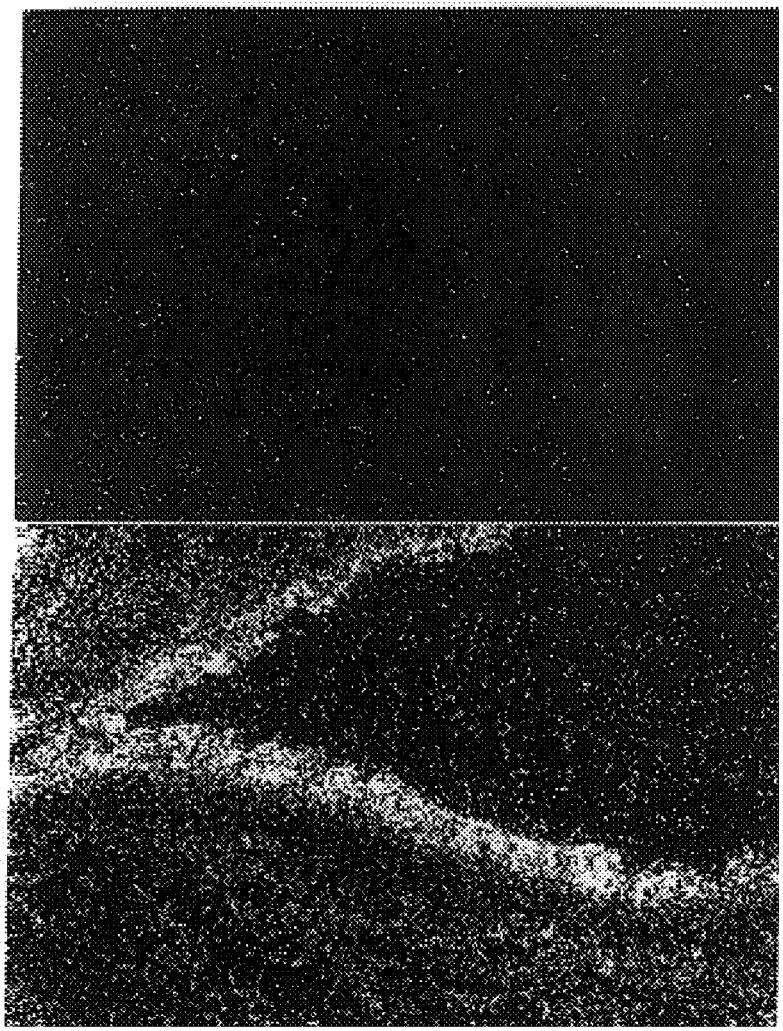
FIGS. 14A and 14B. In situ hybridizations to lung sections from CC10/IL-5 transgenic mice. An RNA probe specific for IL-5 was hybridized to a transgenic lung section (A). The negative control is shown in the bottom panel (B).
Figures 15A, 15B:
FIGS. 15A and 15B. In situ hybridizations to lung sections of a large airway from CC10/IL-5 transgenic mice. An RNA probe specific for IL-5 was hybridized to a transgenic lung section (A). This section shows the intense staining of the lung bronchial airway epithelium. The negative control is shown in the bottom panel (B).
Figures 16A, 16B:
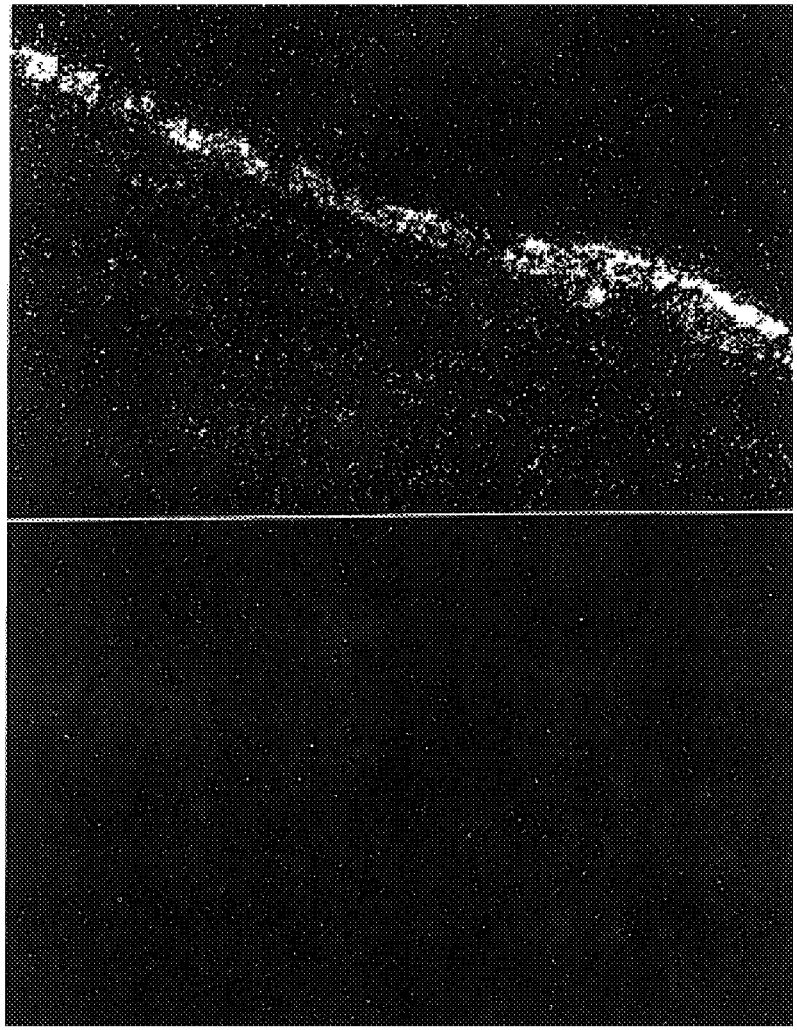
FIGS. 16A and 16B. In situ hybridizations to lung sections from CC10/IL-5 transgenic mice. An RNA probe specific for IL-5 was hybridized to a transgenic lung section (A). This section shows the intense staining of the lung bronchial airway epithelium. The negative control is shown in the bottom panel (B).

The suggestion that the histopathologies result from age dependent immune changes is supported by the data of FIG. 8 showing changes in circulating lymphocyte numbers. These data showed that CD3δ driven IL-5 expression resulted in no changes in peripheral T cell number early in life (0–4 months) and only a 3–5 fold increase in B cell numbers. However, as the mice get older (6–12 months) lymphocyte numbers suddenly increased so that by 12 months of age T cell levels had expanded 3–5 fold above wild-type levels and B cell populations had increased >30-fold. These changes correlate well with the onset of histopathologies.

Regardless of the mechanism(s) inducing the observed pathologies, the data presented here demonstrate that the constitutive expression of IL-5 in a cell type and peripheral location that are endogenous sites of expression in disease states replicates many of the observed hematopoietic and pathologic changes associated with an eosinophil-mediated TH2 type inflammatory reaction.

EXAMPLE X

IL-5 Induced Changes in Lymphocyte Cell Numbers

Previous studies of IL-5 effector functions in the mouse have suggested that this cytokine also induced changes in B cell activity. In addition, other studies have shown that aberrant expression of another TH2 associated cytokine, IL-4, results in significant changes in T cell activity. In an attempt to correlate induced changes in lymphocyte cell numbers with the onset and progression of the observed histopathologies, specific changes in peripheral lymphocyte populations were assessed by FACS analysis on venal blood. These experiments were designed to assess the absolute changes in peripheral blood B and T lymphocytes. Peripheral T cells were identified by the presence of the cell surface protein CD3 and mature B cells were identified by the presence of the marker B220. The observed absolute changes in cell number of each lymphocyte population as a function of postpartum age is graphically displayed in FIG. 4.

In wild-type mice, circulating CD3 positive (T cells) and B220 positive (B cells) lymphocyte numbers were approximately the same and changed only nominally with the age of the mice. In general, the basal level of each lymphocyte type ranged from $3–5 \times 10^3$ cells/mm$^3$ of blood. In NJ.1638 mice the data found in FIG. 4 showed that constitutive systemic expression of IL-5 induced age dependent changes in the numbers of each lymphocyte population. T cell numbers, for example, appeared to be initially (0–4 months of age) unaffected (relative to wild-type) by elevated levels of IL-5. The absolute number of T cells, however, increased after 4 months of age in NJ.1638 animals such that by 7 months of age these animals had T cell numbers equal to 22,000 cells/mm$^3$ of blood, a 6-fold increase from pre-4 month (and wild-type) levels. The number of T cells further increased only slightly in older mice, reaching an upper limit of 28,000 T cells/mm$^3$ of blood.

The effects of thymocyte/peripheral T cell specific IL-5 expression on B lymphocyte populations in these mice was dramatic in magnitude, affecting even very young animals. By one month of age, B cell numbers had increased to 16,000 cells/mm$^3$ of blood (i.e., 4.5-fold increase as compared to wild-type). This elevation in B cell numbers continued throughout the life of the animals increasing to more than 100,000 B cells/mm$^3$ of blood in animals >12 months of age (i.e., a >30-fold increase over wild-type animals).

These data show that the early increases in circulating lymphocyte numbers of NJ.1638 mice (0–4 months of age)

were almost exclusively due to increases in the B cell compartment. In addition, during the age period when both T and B cell numbers are rapidly increasing (6–12 months) the rate of B cell increase far exceeds the rate of T cell accumulation. As a result, instead of contributing equal numbers of cells to the lymphocyte population, older transgenic mice accumulated 4-fold higher numbers of B cells relative to the corresponding T cell pool. These data provide a suggestive correlative relationship between changes in lymphocyte populations and the age dependent development of histopathologies in NJ.1638 mice.

EXAMPLE XI

IL-5 Induced Changes in Transgenic Mice with IL-5 Linked to a Lung Specific Promoter Because elevated levels of IL-5 have been correlated with allergic reactions, a 2.3 kb restriction fragment from the 5' flanking region of the CC10 gene, the "CC10 transcription control sequence," was linked to the IL-5 mingene described above to direct expression of IL-5 in Clara cells of the lung epithelium. This construct was injected into fertilized embryos which were subsequently transferred into the oviduct of a foster mother. Mice born to these foster mothers were screened by DNA analysis for the presence of the CC10/IL-5 transgene. Three distinct transgenic mice were identified and bred to wild-type mice. Blood counts and compositions and histology sections from the lungs of these mice revealed that all three lines showed increased eosinophil numbers in both the blood and lung. One of these lines was chosen for further study.

The CC10/IL-5 transgenic mice showed elevated levels of IL-5 in the serum and bronchial alveolar lavage (BAL) fluid (determined by ELISA as described above, Table 6), elevated total WBC, and elevated numbers of eosinophils in both the blood and lung epithelia. Measurements of bronchial hyperreactivity in response to methacholine challenge indicated that transgenic mice show increased hyperreactivity relative to nontransgenic mice.

TABLE 6

| BAL   | 7 month | 12.5 µg/lavage | 14.8 ± µg/lavage |
|-------|---------|----------------|------------------|
|       |         | 10.1 µg/lavage |                  |
|       |         | 19.8 µg/lavage |                  |
|       |         | 16.7 µg/lavage |                  |
| Serum | 7 month | 1046 pg/ml     | 1333 ± 653 pg/ml |
|       |         | 508 pg/ml      |                  |
|       |         | 1434 pg/ml     |                  |
|       |         | 1057 pg/ml     |                  |
|       |         | 1497 pg/ml     |                  |
|       |         | 2455 pg/ml     |                  |
| Serum | 2 month | 1978 pg/ml     | 1861 ± 169 pg/ml |
|       |         | 1792 pg/ml     |                  |
|       |         | 1815 pg/ml     |                  |
|       |         | 1644 pg/ml     |                  |
|       |         | 2078 pg/ml     |                  |

Discussion

An important conclusion from all of the available transgenic studies of ectopic IL-5 expression is that this cytokine predominantly effects steady-state levels of peripheral eosinophils. The data presented herein, however, also suggest that IL-5 has additional regulatory effects on eosinophils and other cell populations if constitutively expressed in a spatial, temporal, and cell-type specific manner closely analogous to endogenous IL-5 expression.

Moreover, the data suggests that this cytokine is a key component of possible immune-mediated inflammatory pathways leading to the development of destructive physiological changes. The expression of IL-5 in thyrnocytes and peripheral T cell populations resulted in dramatic changes in peripheral WBC numbers with particular effects on circulating eosinophils. The effects of constitutive IL-5 expression, however, were not limited to eosinophil populations. Substantive increases were demonstrated in all WBC populations, including a >30-fold augmentation of B220+B-lymphocyte populations. Deregulated peripheral expression of IL-5 also induced several physiological changes in these mice characterized by the infiltration and/or expansion of eosinophil populations at several extramedullary sites. The effects on extramedullary eosinophilopoiesis were particularly striking and were responsible for most of the increases found in mature eosinophil numbers. The consequences of these IL-5 mediated changes resulted in the development of several unique histopathologies leading to severe pathophysiologic changes and premature death.

The effects on circulating eosinophil numbers shown in NJ.1638 mice greatly exceeded the observed effects found in other transgenic mice expressing this cytokine at similar or even higher IL-5 serum levels. Data were presented which show that this enormous and somewhat specific increase in eosinophil numbers is most likely the result of at least two regulatory effects that can be associated with IL-5 and its expression from a peripheral lymphocyte population.

Data presented in FIG. 6 are an in vivo demonstration of the kinetic effects of IL-5 on progenitor cell populations and lineage committed cell types. These data confirm several of the conclusions derived from in vitro hematopoietic assays and definitively show that IL-5 has little to no effect on uncommitted granulocytic progenitor cell populations (Class I cells using the nomenclature presented here).

IL-5 was also shown to have only nominal effects in the numbers of very early eosinophil-committed progenitor cell types (Class II cells). The data presented hereinabove clearly demonstrate that only more mature eosinophil-committed cell types (Class III and Class IV cells) respond mitogenically to IL-5 stimulation. These observations provide in part the mechanism for the eosinophil-specific effects of IL-5 expression: other cell types may respond (directly or indirectly) to IL-5, however, those effects are small compared to the mitogenic effects this cytokine has on eosinophil-committed progenitor cells.

The extent of extramedullary eosinophilopoiesis found in NJ.1638 mice was shown to be extensive and primarily responsible for the extreme elevations of total cell number. In addition, using the appearance of steady-state mRNA for eosinophil granule protein genes as a measure for eosinophil-conunitted poetic activity (FIGS. 7A–7D), it was shown that extramedullary eosinophilopoiesis was not restricted to the spleen but also occurred in nearly all organ systems and tissue types. These data may reflect a critical function of IL-5 as a mediator of eosinophil numbers through the expansion of extramedullary sites of poises.

An extension of this hypothesis also may explain the unique expansion of WBC numbers in compartments such as the peritoneal cavity that occur in NJ.1638 mice. If lymphocytes provide the key inflammatory signals to indicate a parasitic infestation of this compartment, then stimulation of this pathway would lead to the recruitment of WBC and the differential expansion of eosinophil numbers. Data presented in FIGS. 2A and 2B showed that CD3δ-driven IL-5 expression induces the expansion of WBC numbers to levels associated with an active *M. corti* helminthic infestation of this compartment; this expansion also included the differential recruitment of eosinophils. This observation is unique to the IL-5 transgenic mice described here and is probably a consequence of IL-5 expression from a cell type and location that is consistent with endogenous expression of this signal during an immune response.

The proliferation of WBC, the expansion of eosinophil numbers and recruitment of additional sites of extramedullary eosinophilopoiesis lead to a series of debilitating histopathological changes that ultimately compromise the health and life of these animals. These changes include the uncontrolled growth of the spleen as a function of age and the extensive infiltration of the liver by WBC (especially eosinophils) in transgenic animals of all age groups. Some of the physiological changes are dramatic but produce no observed phenotype. For example, IL-5 expression substantially curtails marrow derived erythropoiesis and shifts this process to an extramedullary site (spleen). As a result, despite this potentially pathophysiologic change, red blood cell counts in transgenic animals showed little change from wild type mice.

In summary, transgenic mice expressing IL-5 under the control of cell-type specific promoters developed unique pathophysiological changes and histopathologies specific to the site of IL-5 expression. In each case, the effects were accompanied by an expansion of peripheral blood eosinophil numbers, the establishment of extramedullary eosinophilopoeisis, and tissue-specific infiltration. The site of IL-5 expression is believed to be an important determinant of tissue-specific eosinophil infiltration and the establishment of inflammatory responses involving eosinophils.

All publications and patents are incorporated by reference herein, as though individually incorporated by reference. The invention is not limited to the exact details shown and described, for it should be understood that many variations and modifications may be made while remaining within the spirit and scope of the invention defined by the claims.

What is claimed is:

1. A transgenic mouse whose cells contain a chimeric DNA sequence, said chimeric DNA sequence comprising:
a thymocyte and/or mature T-cell specific transcription control sequence and a DNA segment which encodes interleukin-5 but lacks endogenous interleukin-5 control sequences which are 5' to the interleukin-5 coding sequence, wherein the thymocyte and/or mature T cell specific transcription control sequence and the DNA segment which encodes interleukin-5 are operatively linked to each other and are integrated into the genome of the mouse, and wherein the DNA segment is expressed in the transgenic mouse so as to result in said mouse exhibiting increased amounts of interleukin-5, increased total white blood cells, an increased number of eosinophils, and at least one of the pathologies selected from the group consisting of premature death, loss of hair, development of skin lesions, enlarged lymph nodes, and rectal prolapse.

2. The transgenic mouse of claim 1 wherein the thymocyte and/or mature T cell specific transcription control sequence is expressed constitutively during T cell differentiation.

3. The transgenic mouse of claim 1 wherein the thymocyte and/or mature T cell specific transcription control sequence comprises CD3δ.

4. The transgenic mouse of claim 3 wherein the thymocyte and/or mature T cell specific transcription control sequence comprises murine CD3δ.

5. The transgenic mouse of claim 1 wherein the DNA segment encodes murine interleukin-5.

6. The transgenic mouse of claim 1 wherein the chimeric DNA sequence comprises pIL-5.EXP.

7. The transgenic mouse of claim 1 wherein the interleukin-5 encoded by the DNA segment is expressed in the serum of the transgenic mouse in an amount of interleukin-5 that is at least fifty times greater than the amount of interleukin-5 in the serum of a corresponding nontransgenic mouse.

8. A transgenic mouse whose cells contain a chimeric DNA sequence, said chimeric DNA sequence comprising:
a lung specific transcription control sequence and a DNA segment which encodes interleukin-5, wherein the lung specific transcription control sequence and the DNA segment which encodes interleukin-5 are operatively linked to each other and are integrated into the genome of the mouse, wherein the DNA segment that encodes interleukin-5 lacks endogenous interleukin-5 control sequences which are 5' to the interleukin-5 coding sequence, wherein the interleukin-5 encoded by the DNA segment is expressed in the transgenic mouse in an amount of interleukin-5 that is at least about fifty times greater than the amount of interleukin-5 in a corresponding nontransgenic mouse, and wherein said mouse exhibits increased amounts of interleukin-5 in bronchial alveolar lavahe fluid and serum, increased total whit blood cells, an increased number of eosinophils, and increased hyperreactivity in response to methachloine challenge, to a corresponding nontransgenic mouse.

9. The transgenic mouse of claim 8 wherein the chimeric DNA sequence is expressed in the Clara cells of the lung.

10. The transgenic mouse of claim 8 wherein the DNA segment encodes murine interleukin-5.

11. An expression cassette comprising a DNA segment encoding interleukin-5, which segment lacks endogenous interleukin-5 control sequences that are 5' to the interleukin-5 coding sequence, operably linked to a thymocyte and/or mature T cell specific transcription control sequence.

12. The expression cassette of claim 11 wherein the thymocyte and/or mature T cell specific transcription control sequence comprises CD3δ.

13. An expression cassette comprising a DNA segment encoding interleukin-5 operably linked to a lung specific transcription control sequence, wherein the DNA segment that encodes interleukin-5 lacks endogenous interleukin-5 control sequences which are 5' to the interleukin-5 coding sequence.

14. The expression cassette of claim 13 wherein the lung specific transcription control sequence is expressed in the Clara cells of the lung.

15. A method for tissue-specific expression of interleukin-5, comprising expressing a chimeric DNA sequence in the cells of a transgenic mouse, wherein the chimeric DNA sequence comprises a thymocyte and/or mature T cell specific transcription control sequence operatively linked to a DNA segment which encodes interleukin-5, wherein the DNA segment lacks any endogenous interleukin-5 control sequences which are 5' to the interleukin-5 coding sequence, wherein the chimeric DNA sequence is integrated into the genome of the mouse, and wherein the DNA segment is expressed in the transgenic mouse so as to result in said mouse exhibiting increased amounts of interleukin-5, increased total white blood cells, an increased number of eosinophils, and at least one of the pathologies selected from the group consisting of premature death, loss of hair, development of skin lesions, enlarged lymph nodes, and rectal prolapse.

16. A method according to claim 15 wherein the interleukin-5 encoded by the DNA segment is expressed in the serum of the transgenic mouse in an amount of interleukin-5 that is at least fifty times greater than the amount of interleukin-5 in the serum of a corresponding nontransgenic mouse.

17. A method of using a transgenic mouse to screen for an agent that reduces or inhibits an interleukin-5 associated pathology, comprising:

(a) administering the agent to the transgenic mouse, wherein the transgenic mouse comprises a chimeric DNA sequence comprising a thymocyte and/or mature T cell specific transcription control sequence operatively linked to a DNA segment which encodes interleukin-5, wherein the DNA segment lacks any endogenous interleukin-5 control sequences which are 5' to the interleukin-5 coding sequence, wherein the chimeric DNA sequence is integrated into the genome of the mouse, and wherein the DNA segment is expressed as interleukin-5 in the transgenic mouse "so as to result in an interleukin-5 associated pathology" has been inserted after the phrase "interleukin-5 in the transgenic mouse"; and (b) determining whether said agent reduces or inhibits an interleukin-5 associated pathology in the transgenic mouse relative to a transgenic mouse of step (a) which has not been administered the agent.

18. A method for tissue-specific expression of interleukin-5, comprising expressing a chimeric DNA sequence in the cells of a transgenic mouse, wherein the chimeric DNA sequence comprises a lung specific transcription control sequence operatively linked to a DNA segment which encodes interleukin-5, wherein the chimeric DNA sequence is integrated into the genome of the mouse, wherein the DNA segment that encodes interleukin-5 lacks endogenous interleukin-5 control sequences which are 5' to the interleukin-5 coding sequence, wherein the DNA segment is expressed in the transgenic mouse in an amount of interleukin-5 that is at least about fifty times greater than the amount of interleukin-5 in a corresponding nontransgenic mouse, and wherein said mouse exhibits increased amounts of interleukin-5 in bronchial alveolar lavage fluid and serum, increased total white blood cells, an increased number of eosinophils, and increased hyperreactivity in response to methacholine challenge, relative to a corresponding nontransgenic mouse.

19. A method of using a transgenic mouse to screen for an agent that reduces or inhibits interleukin-5 associated pathologies, comprising:

(a) administering the agent to the transgenic mouse, wherein the transgenic mouse comprises a chimeric DNA sequence comprising a lung specific transcription control sequence operatively linked to a DNA segment which encodes interleukin-5, wherein the chimeric DNA sequence is integrated into the genome of the mouse, wherein the DNA segment that encodes interleukin-5 lacks endogenous interleukin-5 control sequences which are 5' to the interleukin-5 coding sequence, and wherein the DNA segment is expressed as interleukin-5 in the transgenic mouse so as to result in an interleukin-5 associated pathology; and (b) determining whether said agent reduces or inhibits interleukin-5 associated pathology in the transgenic mouse relative to a transgenic mouse of step (a) which has not been administered the agent.

* * * * *

UNITED STATES PATENT AND TRADEMARK OFFICE
CERTIFICATE OF CORRECTION

PATENT NO. : 6,025,539
DATED : February 15, 2000
INVENTOR(S) : Lee et al.

Page 1 of 1

It is certified that error appears in the above-identified patent and that said Letters Patent is hereby corrected as shown below:

Column 17,
Lines 1 & 2, delete "FIG. 4(A)" and insert "FIGS. 4A and 4B" therefor.

Column 41,
Line 5, delete "whit" and insert "white", therefor.

Column 42,
Lines 9 & 10, delete the qoutation marks before "so" and after "pathology".
Lines 11 & 12, delete "has been inserted after the phrase "interleukin-5 in the transgenic mouse"".

Signed and Sealed this

Twenty-eighth Day of August, 2001

Attest:

NICHOLAS P. GODICI
Attesting Officer    Acting Director of the United States Patent and Trademark Office